United States Patent [19]

Gruber et al.

[11] Patent Number: 5,658,889

[45] Date of Patent: Aug. 19, 1997

[54] METHOD AND COMPOUNDS FOR AICA RIBOSIDE DELIVERY AND FOR LOWERING BLOOD GLUCOSE

[75] Inventors: Harry E. Gruber, San Diego; Ronald R. Tuttle, Escondido; Clinton E. Browne, Oceanside; Bheemarao G. Ugarkar, Escondido; Jack W. Reich, Carlsbad; Ernest K. Metzner, Del Mar; Paul J. Marangos, Encinitas, all of Calif.

[73] Assignee: Gensia Pharmaceuticals, Inc., San Diego, Calif.

[21] Appl. No.: 355,836

[22] Filed: Dec. 14, 1994

Related U.S. Application Data

[63] Continuation of Ser. No. 230,421, Apr. 19, 1994, abandoned, which is a continuation of Ser. No. 466,979, Jan. 18, 1990, abandoned, which is a continuation-in-part of Ser. No. 301,453, Jan. 24, 1989, Pat. No. 5,200,525, and Ser. No. 408,107, Sep. 15, 1989, abandoned, which is a continuation-in-part of Ser. No. 301,222, Jan. 24, 1989, Pat. No. 5,082,829.

[51] Int. Cl.$^6$ .................................................. A61K 31/70
[52] U.S. Cl. ................................ 514/43; 514/45; 514/46; 514/866
[58] Field of Search .................................. 514/45, 46, 47, 514/866, 884, 886

[56] References Cited

U.S. PATENT DOCUMENTS

| | | | |
|---|---|---|---|
| 4,912,092 | 3/1990 | Gruber | 514/45 |
| 4,943,629 | 7/1990 | De Vries et al. | 536/117 |
| 4,968,790 | 11/1990 | De Vries et al. | 514/23 |

FOREIGN PATENT DOCUMENTS

| | | |
|---|---|---|
| 0 372 157 | 6/1990 | European Pat. Off. . |
| 0 455 006 A2 | 11/1991 | European Pat. Off. . |

*Primary Examiner*—J Wilson
*Attorney, Agent, or Firm*—Lyon & Lyon LLP

[57] ABSTRACT

AICA riboside and prodrugs of AICA riboside are provided which lower blood glucose for the treatment of various pathologic conditions, including hypoglycemia, insulin deficiency, insulin resistance diabetes and Syndrome X. Prodrugs of AICA riboside provide AICA riboside in an orally bioavailable form. The use of adenosine kinase inhibition and ZMP enhancement for lowering blood glucose are also described.

22 Claims, 16 Drawing Sheets

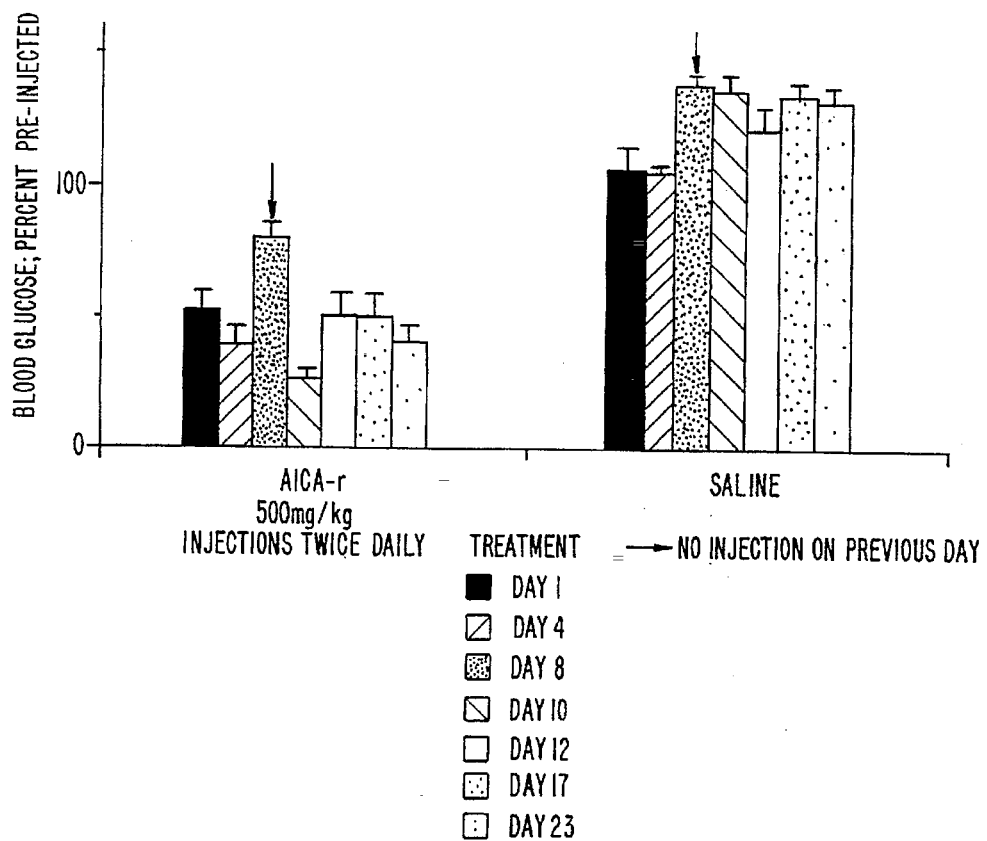
FIG. 22.
FIG. 23.
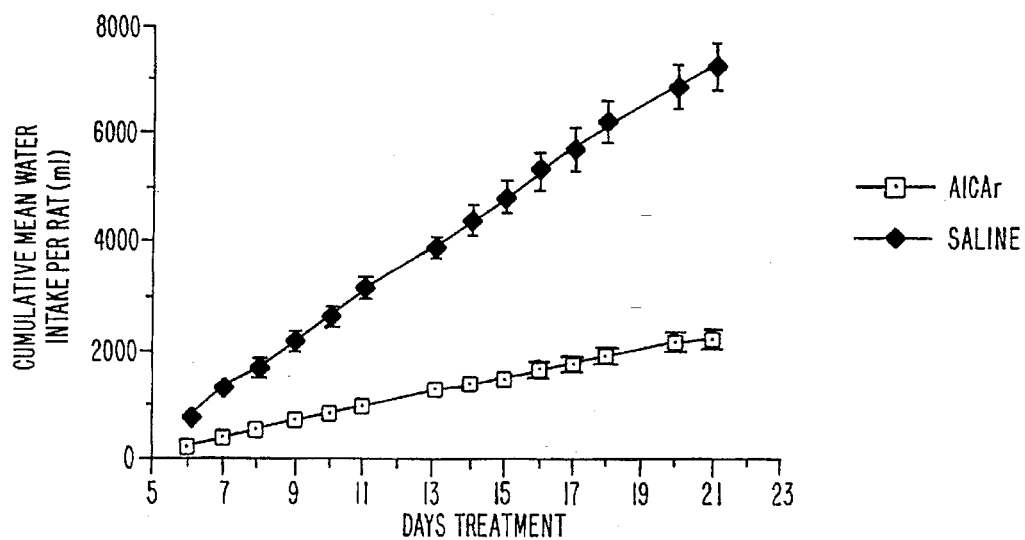

METHOD AND COMPOUNDS FOR AICA RIBOSIDE DELIVERY AND FOR LOWERING BLOOD GLUCOSE

RELATED APPLICATIONS

This is a continuation of application Ser. No. 08/230,421, filed Apr. 19, 1994 now abandoned, which application is a continuation of application Ser. No. 07/466,979, filed Jan. 18, 1990 now abandoned, which application is a continuation-in-part of Ser. No. 301,453, filed Jan. 24, 1989, U.S. Pat. No. 5,200,525 and of application Ser. No. 408,107, filed Sep. 15, 1989 now abandoned which is a continuation-in-part of application Ser. No. 301,222, U.S. Pat. No. 5,082,829 filed Jan. 24, 1989.

FIELD OF THE INVENTION

This invention generally relates to purine nucleosides, especially to 1-β-D-ribofuranosyl-5-amino-imidazole-4-carboxamide ("5-amino-4-imidazolecarboxamide riboside" or "AICA riboside") prodrugs. It also relates to the preparation, use and administration of these compounds which, when introduced into the body, will metabolize into their active forms. This invention also relates to ischemic syndrome treatments, anticonvulsant therapeutic agents, methods and treatment of seizure and related disorders, and to lowering blood glucose and the treatment of blood glucose-related disorders including diabetes mellitus.

BACKGROUND OF THE INVENTION

The present invention is directed to compounds which act as prodrugs of AICA riboside and certain analogs of it. AICA riboside monophosphate is a naturally occurring intermediate in purine biosynthesis. AICA riboside is also naturally occurring and is now known to enable adenosine release from cells during net ATP catabolism. By virtue of its adenosine releasing abilities, AICA riboside has many therapeutic uses. However, we have discovered that AICA riboside does not cross the blood-brain barrier well and is inefficiently absorbed from the gastrointestinal tract; both characteristics decrease its full potential for use as a therapeutic agent.

We have also discovered that AICA riboside, and AICA riboside pro-drugs and analogs can be used to lower blood glucose levels in animals, including rats, rabbits, dogs and man. These compounds are surprisingly efficacious for lowering blood sugar and are believed to be partially causing their effect by decreasing hepatic gluconeogenesis. These compounds will be useful for the treatment of animals for conditions including hyperglycemia, insulin resistance, insulin deficiency, diabetes mellitis, Syndrome X, to control the hyperglycemia and/or hyperlipidemia associated with total parenteral nutrition, or a combination of these effects. While AICA riboside does not have the enhanced bioavailability as described for those pro-drugs set forth herein as useful for penetrating the gut barrier, it may be nevertheless useful for the above conditions because AICA riboside itself will be present in amounts sufficient to reach the liver, as we have also discovered. AICA riboside monophosphate is implicated by our studies to be the causative agent and, accordingly, it and monophosphate forms of prodrug and analog compounds noted herein are within the scope of our invention.

Adenosine, 9-β-D-ribofuranosyladenine (the nucleoside of the purine adenine), belongs to the class of biochemicals termed purine nucleosides and is a key biochemical cell regulatory molecule, as described by Fox and Kelly in the *Annual Reviews of Biochemistry*, Vol. 47, p. 635, 1978.

Adenosine interacts with a wide variety of cell types and is responsible for a myriad of biological effects. Adenosine serves a major role in brain as an inhibitory neuromodulator (see Snyder, S. H., *Ann. Rev. Neural Sci.* 8:103–124 1985, Marangos, et al., *NeuroSci and Biobehav. Rev.* 9:421–430 (1985), Dunwiddie, *Int. Rev. Neurobiol.*, 27:63–130 (1985)). This action is mediated by ectocellular receptors (Londos et al., *Regulatory Functions of Adenosine*, pp. 17–32 (Berne et al., ed.) (1983)). Among the documented actions of adenosine on nervous tissue are the inhibition of neural firing (Phillis et al., *Europ. J. Pharmacol.*, 30:125–129 (1975)) and of calcium dependent neurotransmitter release (Dunwiddie, 1985). Behaviorally, adenosine and its metabolically stable analogs have profound anticonvulsant and sedative effects (Dunwiddie et al., *J. Pharmacol. and Exptl. Therapeut.*, 220:70–76 (1982); Radulovacki et al., *J. Pharmacol. Exptl. Thera.*, 228:268–274 (1981)) that are effectively reversed by specific adenosine receptor antagonists. In fact, adenosine has been proposed to serve as a natural anticonvulsant, and agents that alter its extracellular levels are modulators of seizure activity (Dragunow et al., *Epilepsia* 26:480–487 (1985); Lee et al., *Brain Res.*, 21:1650–164 (1984)). In addition, adenosine is a potent vasodilator, an inhibitor of immune cell function, an inhibitor of granulocyte oxygen free radical production, an anti-arrhythmic, and an inhibitory neuromodulator. Given its broad spectrum of biological activity, considerable effort has been aimed at establishing practical therapeutic uses for adenosine and its analogs.

Since adenosine is thought to act at the level of the cell plasma membrane by binding to receptors anchored in the membrane, past work has included attempts to increase extra-cellular levels of adenosine by administering it into the blood stream. Unfortunately, because adenosine is toxic at concentrations that have to be administered to a patient to maintain an efficacious extracellular therapeutic level, the administration of adenosine alone is of limited therapeutic use. Further, adenosine receptors are subject to negative feedback control following exposure to adenosine, including down-regulation of the receptors.

Other ways of achieving the effect of a high local extracellular level of adenosine exist and have also been studied. They include: a) interference with the uptake of adenosine with reagents that specifically block adenosine transport, as described by Paterson et al., in the *Annals of the New York Academy of Sciences*, Vol. 255, p. 402 (1975); b) prevention of the degradation of adenosine, as described by Carson and Seegmiller in *The Journal of Clinical Investigation*, Vol. 57, p. 274 (1976); and c) the use of analogs of adenosine constructed to bind to adenosine cell plasma membrane receptors.

There are a large repertoire of chemicals that can inhibit the cellular uptake of adenosine. Some do so specifically, and are essentially competitive inhibitors of adenosine uptake, and others inhibit nonspecifically. P-nitrobenzylthioinosine and dipyridamole appear to be competitive inhibitors. A variety of other chemicals, including colchicine, phenethylalcohol and papaverine inhibit uptake nonspecifically.

Extracellular levels of adenosine can be increased by the use of chemicals that inhibit enzymatic degradation of adenosine. Previous work has focused on identifying inhibitors of adenosine deaminase, which participates in the conversion of adenosine to inosine. Adenosine deaminase activity is inhibited by coformycin, 2'-deoxycoformycin, and erythro-9-(2-hydroxy-3-nonyl) adenine hydrochloride.

A number of adenosine receptor agonists and antagonists have been generated having structural modifications in the purine ring, alterations in substituent groups attached to the purine ring, and modifications or alterations in the carbohydrate moiety. Halogenated adenosine derivatives appear to have been promising as agonists or antagonists and, as described by Wolff et al. in the *Journal of Biological Chemistry*, Vol. 252, p. 681, 1977, exert biological effects in experimental systems similar to those caused by adenosine. Derivatives with N-6 or 5'-substitutions have also shown promise.

Although all three techniques discussed above may have advantages over the use of adenosine alone, they have been found to have several disadvantages. The major disadvantages of these techniques are that they rely on chemicals that have adverse side effects, primarily due to the fact that they must be administered in doses that are toxic, and that they affect most cell types nonselectively. As described in *Purine Metabolism in Man*, (eds. De Baryn, Simmonds and Muller), Plenum Press, New York, 1984, most cells in the body carry receptors for adenosine. Consequently the use of techniques that increase adenosine levels generally throughout the body can cause unwanted, dramatic changes in normal cellular physiology. In addition, adenosine deaminase inhibitors prevent the degradation of deoxyadenosine which is a potent immunotoxin. (Gruber et al., *Ann. New York Acad. Sci.* 451:315–318 (1985)).

It will be appreciated that compounds which increase extracellular levels of adenosine or adenosine analogs at specific times during a pathologic event, without complex side effects, and which would permit increased adenosine levels to be selectively targeted to cells that would benefit most from them, would be of considerable therapeutic use. By way of example, such compounds would be especially useful in the prevention of, or response during, an ischemic event, such as heart attack or stroke, or other event involving an undesired restricted or decreased blood flow, such as atherosclerosis or skin flap surgery, for adenosine is a vasodilator and prevents the production of superoxide radicals by granulocytes. Such compounds would also be useful in the prophylactic or affirmative treatment of pathologic states involving increased cellular excitation, such as (1) seizures or epilepsy, (2) arrhythmias (3) inflammation due to, for example, arthritis, autoimmune disease, Adult Respiratory Distress Syndrome (ARDS), and granulocyte activation by complement from blood contact with artificial membranes as occurs during dialysis or with heart-lung machines. It would further be useful in the treatment of patients who might have chronic low adenosine such as those suffering from autism, cerebral palsy, insomnia and other neuropsychiatric symptoms, including schizophrenia. The compounds useful in the invention may be used to accomplish these ends.

Clearly, there is a need for more effective anticonvulsant therapeutic compounds and strategies since most of the currently used antiseizure agents are toxic (e.g., dilantin), or are without efficacy in many patients. Adenosine releasing agents, which enhance adenosine levels during net ATP catabolism will be useful for the treatment of seizure disorders.

Compounds which selectively increase extracellular adenosine will also be used in the prophylactic protection of cells in the hippocampus implicated in memory. The hippocampus has more adenosine and glutamate receptors than any other area of the brain. Accordingly, as described below, it is most sensitive to stroke or any condition of low blood flow to the brain. Some recent studies support the theory that Alzheimer's disease may result from chronic subclinical cerebral ischemia. The compounds of the invention will be used for the treatment and/or prevention of both overt stroke and Alzheimer's disease.

It is now established that relatively short periods of brain ischemia (on the order of 2 to 8 minutes) set into motion a series of events that lead to an eventual death of selected neuronal populations in brain. This process is called delayed excitotoxicity and it is caused by the ischemia-induced release of the excitatory amino acid (EAA) neurotransmitters glutamate and aspartate. Within several days post-stroke the neurons in the brain are overstimulated by EAA's to the point of metabolic exhaustion and death. Because glutamate appears to be the major factor involved in post-stroke cell damage, the blockade of glutamate receptors in brain could be beneficial in stroke therapy. In animals, glutamate receptor blockers have been shown to be effective in alleviating or reversing stroke associated neural damage. These receptor blockers have, however, been shown to lack specificity and produce many undesirable side effects. Church, et al., "Excitatory Amino Acid Transmission," pp. 115–118 (Alan R. Liss, Inc. 1987).

Adenosine has been shown to be a potent inhibitor of glutamate release in brain. The CA-1 region of brain is selectively sensitive to post-stroke destruction. In studies, where observations were made at one, three and six days post-stroke the CA-1 area was shown to be progressively destroyed over time. However, where cyclohexyladenosine ("CHA") a global adenosine agonist, was given shortly after the stroke, the CA-1 area was markedly protected. (Daval et al., *Brain Res.* 491: 212–226 (1989).) That beneficial effect was also seen in the survival rate of the animals. Because of its global effect, however, CHA has non-specific side effects. For example it undesirably will lower blood pressure and could remove blood from the ischemic area, thereby causing further decreased blood flow.

The compounds of the invention described and claimed herein not only show the beneficial adenosine release (glutamate inhibiting properties) but are both site and event specific, avoiding the unwanted global action of known adenosine agonists. These compounds will also be used in the treatment of neurodegenerative diseases related to the exaggerated action of excitatory amino acids, such as Parkinson's disease.

Another area of medical importance is the treatment of neurological diseases or conditions arising from elevated levels of homocysteine (e.g., vitamin B12 deficiencies). The novel AICA riboside prodrugs of this invention may be used for such purposes as well.

A further area of medical importance is the treatment of allergic diseases, which can be accomplished by either preventing mast cell activation, or by interfering with the mediators of allergic responses which are secreted by mast cells. Mast cell activation can be down-regulated by immunotherapy (allergy shots) or by mast cell stabilizers such as cromalyn sodium, corticosteroids and aminophylline. There are also therapeutic agents which interfere with the products of mast cells such as anti-histamines and adrenergic agents. The mechanism of action of mast cell stabilization is not clearly understood. In the case of aminophylline it is possible that it acts as an adenosine receptor antagonist. However, agents such as cromalyn sodium and the corticosteroids are not as well understood.

It will be appreciated, therefore, that effective allergy treatment with compounds which will not show any of the side effects of the above noted compounds, such as drowsiness in the case of the anti-histamines, agitation in the case of adrenergic agents, and Cushing disease symptoms in the case of the corticosteroids would be of great significance and utility. In contrast to compounds useful in the present invention, the AICA riboside prodrugs, none of the three known mast cell stabilizers are known or believed to be metabolized in the cell to purine nucleoside triphosphates or purine nucleoside monophosphates.

The use of AICA riboside and prodrugs of AICA riboside as antiviral agents and for increasing the antiviral activity of AZT is disclosed in commonly-assigned U.S. patent application Ser. No. 301,454, "Antivirals and Methods for Increasing the Antiviral Activity of AZT", filed Jan. 24, 1989, the disclosure of which is incorporated herein by reference.

Certain derivatives of AICA riboside have been prepared and used as intermediates in the synthesis of nucleosides such as adenosine or nucleoside analogs such as 3'-deoxy-thio-AICA riboside. See, e.g., U.S. Pat. No. 3,450,693 to Suzuki et al.; Miyoshi et al., Chem. Pharm. Bull. 24(9): 2089–2093 (1976); Chambers et al., Nucleosides & Nucleotides 7(3): 339–346 (1988); Srivastava, J. Org. Chem. 40(20): 2920–2924 (1975).

Hyperglycemia has been reported to be associated with a poor prognosis for stroke. (Helgason, Stroke 19(8): 1049–1053 (1988). In addition, mild hypoglycemia induced by insulin treatment has been shown to improve survival and morbidity from experimentally induced infarct. (LeMay et al., Stroke 19(11): 1411–1419 (1988)). We believe that AICA riboside and the prodrugs of the present invention will be useful to help protect against ischemic injury to the central nervous system (CNS) at least partly by their ability to lower blood glucose.

Hyperglycemia and related diabetic conditions are generally divided into "type I" or severe (typically insulin requiring) and "type II" or mild (typically controlled by oral hypoglycemic agents and/or diet and exercise). Type I diabetic patients have severe insulin deficiency with complications typically including hyperglycemia and ketoacidosis. Type II diabetic patients typically have milder insulin deficiency or decreased insulin sensitivity associated with hyperglycemia predominantly from accelerated hepatic gluconeogenesis. Both forms of diabetic conditions are associated with atherosclerosis and ischemic organ injury.

Oral hypoglycemic agents that are currently available clinically include sulfonylureas (e.g., tolbutamide, tolazamide, acetohexamide, chlorpropamide, glyburide, glipizide) and biguanides (e.g. phenformin and metformin). The sulfonylurea class of drugs lower blood sugar acutely in man and experimental animals by causing insulin release but in long term studies, their activity appears to involve extra pancreatic effects. These drugs are active on potassium cation channels, but it is not known if this activity is related to their hypoglycemic effects. The sulfonyl-urea class of drugs are not ideal hypoglycemic agents for a variety of reasons; moreover, they have been associated with increased risk of cardiovascular disease and can be of insufficient efficacy for many Type II diabetes patients.

The biguanide class of drugs reduce blood sugar by increasing peripheral utilization of glucose and by decreasing hepatic glucose production, both effects presumably caused by inhibiting oxidative phosphorylation. In addition, because of their inhibition of oxidative phosphorylation, the biguanides have been associated with fatal lactic acidosis and, for that reason, are at present not available clinically in the United States.

Other compounds which lower blood sugar have been described in the literature, but none of them is available clinically due to other toxicities. (See Sherratt, H. S. A., "Inhibition of Gluconeogenesis by Non-Hormonal Hypoglycaemic Compounds" in *Short-Term Regulation of Liver Metabolism*, pp. 199–277 (Hue, L. and Van de Werve, G., ed.s, Elsovier/North Holland Biomedical Press, 1981)). D-Ribose has been reported to cause hypoglycemia after oral or intravenous administration to experimental animals and humans and Foley (*J. Clin. Invest.* 37: 719–735 (1958)) demonstrated an inhibition of phosphoglucomutase by ribose-5'-phosphate (formed intracellularly after ribose therapy). Although others have suggested that ribose lowers glucose via increased insulin release (Ishiwita et al., *Endoncinol. Japan* 25: 163–169 (1978)), the preponderance of evidence favors decreased glucose production over increased insulin release.

Fructose diphosphatase has been suggested as an ideal target for new hypoglycemic agents, since it is one of two control steps in gluconeogenesis. (See, Sherratt, supra 1981) However, therapeutic agents which lower its activity are not presently clinically available. Fructose diphosphatase is inhibited by AMP and activated by ATP, being responsive to the cellular energy charge. Pyruvate carboxylase, the other major regulatory step in gluconeogenesis, is the first committed step towards glucose production and is regulated by the availability of acetyl CoA; however, its inhibition would result in interruption of mitochondrial function.

The present invention is directed to purine prodrugs and analogs which exhibit and, in some cases improve upon, the positive biological effects of AICA riboside and other adenosine releasing compounds without the negative effects of systemic adenosine. The compounds herein defined may be used as prodrugs. The novel compounds typically exhibit one or more of the following improvements over AICA riboside: 1) more potent adenosine releasing effects; 2) increased half-lives; 3) increased brain penetration; 4) increased oral bioavailability; 5) increased myocardial targeting; 6) in some cases efficacy improvements over AICA riboside itself.

The AICA riboside prodrugs of this invention may be used in treatment and prevention of a number of disorders, some of which already have been mentioned.

SUMMARY OF THE INVENTION

The present invention is directed to prodrugs of AICA riboside. We have surprisingly found that AICA riboside has very limited oral bioavailability. Accordingly, we have found that when AICA riboside is given orally, very little or none of it reaches the tissue(s) which comprise its site(s) of action. Among other factors, the present invention is based on our finding that oral administration of prodrugs of AICA riboside result in enhanced levels of AICA riboside in the blood and other tissues, as compared with oral administration of AICA riboside itself. Use of prodrugs of AICA riboside allow for delivery of therapeutically effective amounts of AICA riboside to the tissue(s) to be treated.

AICA riboside has less than full gastrointestinal tract penetration and relatively low blood brain-barrier penetration. Derivatization of adenosine releasing agents, including AICA riboside, has been undertaken with the goals of increasing penetration of AICA riboside into the brain and through the gut by delivering it as a brain and/or gut permeable form that avoids first pass metabolism and, while reaching the target regenerates into the parent compound (a prodrug strategy).

The present invention is directed to compounds which act as prodrugs of AICA riboside and their use as prodrugs in therapies as described below. These prodrug compounds comprise a modified AICA riboside having an AICA ribosyl moiety and at least one hydrocarbyloxycarbonyl or hydrocarbylcarbonyl moiety per equivalent weight of AICA ribosyl moiety.

It has been found that AICA riboside may be chemically modified to yield an AICA riboside prodrug wherein one or more of the hydroxyl oxygens of the ribosyl moiety (i.e. 2'-, 3'- or 5'-) is substituted with a hydrocarbyloxycarbonyl or hydrocarbylcarbonyl moiety.

These compounds function as prodrugs of AICA riboside and are better absorbed from the gastrointestinal system and are better able to cross the blood-brain barrier than AICA riboside itself. It is believed that the added ester side groups allow for improved absorption from the gastrointestinal system and decreased first pass metabolism, as well as in making more drug available for crossing the blood-brain barrier. As the prodrug molecule approaches or reaches the active site, intact modifying groups can be endogenously cleaved to regenerate AICA riboside.

The prodrug compounds of the present invention are useful in treating a variety of clinical conditions where increasing extracellular levels of adenosine would be beneficial. Accordingly, the present invention is directed to the prophylactic and affirmative treatment of such conditions as stroke, Alzheimer's disease, homocysteineuria, skin flap and reconstructive surgery, post-ischemic syndrome and other seizure-related conditions, spinal cord ischemia, intraoperative ischemia especially during heart/lung bypass procedures, cardioplegia, diabetes mellitus, hyperglycemic conditions including that associated with total parenteral nutrition, and myocardial ischemia, including angina and infarct, using these prodrug compounds. These prodrugs are useful in treating other indications where AICA riboside has exhibited activity and where oral administration is preferred or would be advantageous. Thus, they are useful in delivering AICA riboside in an orally bioavailable form. This invention is also directed to pharmaceutical compositions comprising an effective amount of a prodrug compound of the present invention in a pharmaceutically acceptable carrier.

Preferred prodrug compounds include those where at least one of the hydroxyl oxygens of the ribosyl moiety is substituted with a hydrocarbyloxycarbonyl or hydrocarbylcarbonyl moiety. One preferred class of compounds are those wherein at least one hydroxyl oxygen is substituted with a hydrocarbyloxycarbonyl moiety. One preferred class of prodrug compounds comprises compounds wherein either of the 3'- or 5'-hydroxyl oxygens, or both, of the ribosyl moiety is substituted with a hydrocarbyloxycarbonyl or hydrocarbylcarbonyl moiety.

Compounds having a 5'-ester substituent constitute a preferred class of compounds due in part to the slower hydrolysis rates that have been observed in plasma, giving a longer half-life in the bloodstream and, thus, allowing less frequent dosing.

Due to their enhanced oral bioavailability, preferred prodrug compounds include those substituted with 1 to 3 short chain acyl ester groups. In particular, compounds having a 5'-pivaloyl or isobutyryl substitution or having a 2',3',5'-triacetyl substitution have shown enhanced bioavailability when given orally. Also showing enhanced oral bioavailability are compounds having a 5'-butyryl or 3',5'-diacetyl substitutions.

Another preferred group of compounds include those having a 3'-hydrocarbyloxycarbonyl substitution, especially those having an isobutoxycarbonyl or neopentoxycarbonyl substitution.

In one aspect, the present invention is directed to a class of novel prodrug compounds. In general, these compounds comprise a modified AICA riboside having an AICA ribosyl moiety and at least one hydrocarbyloxycarbonyl or hydrocarbylcarbonyl moiety, or combinations thereof, per equivalent weight of AICA ribosyl moiety, provided that said prodrug does not have three acetyl, propionyl or benzoyl moieties per equivalent weight of AICA ribosyl moiety and that it is not dibenzoyl-substituted or mono-acetyl substituted at the 5'-position of the ribosyl moiety.

A particularly preferred group of compounds includes those mono- or di- substituted with a short chain acyl ester group. Such compounds include those having a 5'-acyl ester substitution or a 3',5'-diacyl substitution. Preferred diacyl substituted compounds include the 3',5'-diacetyl substituted compound and the 5'-n-butyryl substituted compound. Especially preferred compounds include those having either a 5'-pivalyl or 5'-isobutyryl substitution.

Another aspect of the present invention provides prodrugs of carbocyclic AICA riboside.

Definitions

As used herein, the following terms have the following meanings, unless expressly stated to the contrary:

The term "alkyl" refers to saturated aliphatic groups, including straight, branched and carbocyclic groups.

The term "alkenyl" refers to unsaturated alkyl groups having at least one double bond [e.g. CH$_3$CH=CH(CH$_2$)$_2$—] and includes both straight and branched-chain alkenyl groups.

The term "alkynyl" refers to unsaturated groups having at least one triple bond [e.g. CH$_3$C≡C(CH$_2$)$_2$—] and includes both straight chain and branched-chain groups.

The term "aryl" refers to aromatic hydrocarbyl and heteroaromatic groups which have at least one aromatic ring.

The term "alkylene" refers to straight and branched-chain alkylene groups which are biradicals, and includes, for example, groups such as ethylene, propylene, 2-methylpropylene

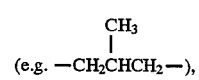

(e.g. —CH$_2$CHCH$_2$—),

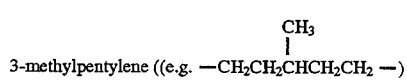

3-methylpentylene ((e.g. —CH$_2$CH$_2$CHCH$_2$CH$_2$ —)

and the like.

The term "hydrocarbyl" denotes an organic radical composed of carbon and hydrogen which may be aliphatic (including alkyl, alkenyl, and alkynyl groups and groups which have a mixture of saturated and unsaturated bonds), alicyclic (carbocyclic), aryl (aromatic) or combinations thereof; and may refer to straight-chained, branched-chain, or cyclic structures or to radicals having a combination thereof, as well as to radicals substituted with halogen atom(s) or heteroatoms, such as nitrogen, oxygen, and sulfur and their functional groups (such as amino, alkoxy, aryloxy, carboxyl, ester, amide, carbamate or lactone groups, and the like), which are commonly found in organic compounds and radicals.

The term "hydrocarbyloxycarbonyl" refers to the group

wherein R' is a hydrocarbyl group.

The term "hydrocarbylcarbonyl" refers to the group

wherein R' is a hydrocarbyl group.

The term "ester" refers to a group having a

linkage, and includes both acyl ester groups and carbonate ester groups.

The term "halo" or "halogen" refers to fluorine, chlorine, bromine and iodine.

The term "carbonate ester" refers to the group

wherein R' is hydrocarbyl or to compounds having at least one such group.

The term "acyl ester" refers to the group

wherein R' is hydrocarbyl or to compounds having at least one such group.

The term "mixed ester" refers to compounds having at least one carbonate ester group and at least one acyl ester group or to compounds having combinations of different acyl ester or carbonate ester groups.

In referring to AICA riboside and the AICA riboside prodrugs of the present invention, the following conventional numbering system for the rings is used:

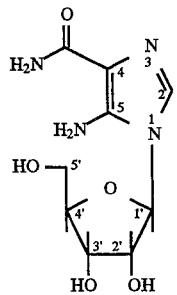

The term "carbocyclic AICA riboside" refers to an analog of AICA riboside wherein the oxygen atom of the ribosyl ring has been replaced by a carbon atom. Accordingly, carbocyclic AICA riboside has the following structure and the following conventional number system for the rings, as noted, is used:

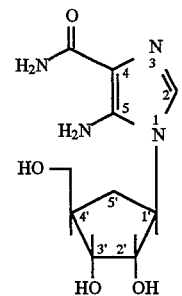

The term "prodrug" refers to compounds which are derivatives of a parent compound (such as AICA riboside) which have been derivativized to assist the parent compound in getting to the desired locus of action. The derivitized portion of the prodrug is cleaved (metabolized) or activated to give the parent compound either in transit or at the desired locus. Typically a prodrug may allow the parent compound to cross or better cross a biological barrier such as the gut epithelium or the blood-brain barrier, at which point it is cleaved to give the parent compound.

The term "oral bioavailability" refers to the quantity of drug reaching the bloodstream after oral administration. Accordingly, an "orally bioavailable" drug is one which is well absorbed from the gut and reaches the blood stream when administered orally.

BRIEF DESCRIPTION OF THE DRAWINGS

FIG. 22 depicts the effect of chronic AICA riboside treatment in streptozotocin-induced diabetic rats.

FIG. 23 depicts the effect of chronic AICA riboside treatment on water consumption by streptozotocin-induced diabetic rats.

DETAILED DESCRIPTION OF THE INVENTION

Preferred Prodrug Compounds

Figure 1:
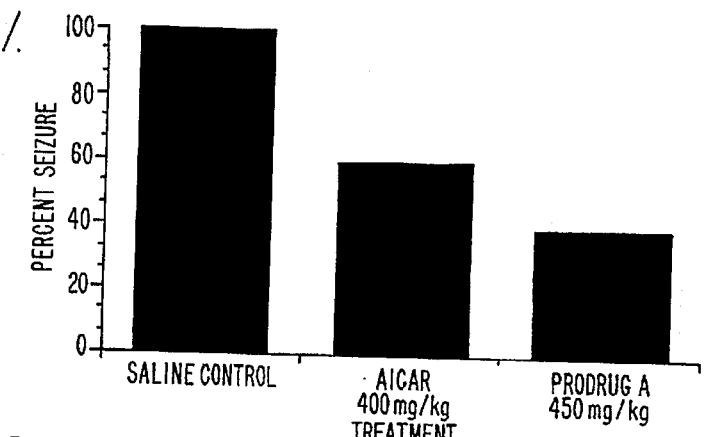
FIG. 1 depicts the activities of AICA riboside and Prodrug A in preventing homocysteine thiolactone-induced seizures in mice.

Preferred prodrug compounds of the present invention comprise a modified AICA riboside having an AICA ribosyl moiety and at least one hydrocarbyloxycarbonyl or hydrocarbylcarbonyl moiety per equivalent weight of AICA ribosyl moiety.

Preferred are AICA riboside prodrugs of the formula:

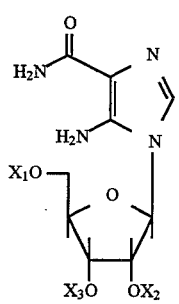

wherein $X_1$, $X_2$ and $X_3$ are independently (a) hydrogen, (b)

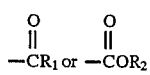

wherein $R_1$ is independently hydrocarbyl or independently mono- or dihydrocarbylamino and $R_2$ is independently hydrocarbyl, or (c) two of $X_1$, $X_2$ and $X_3$ taken together form a cyclic carbonate ring, provided that at least one of $X_1$, $X_2$ and $X_3$ is not hydrogen.

Since for many indications, it would be advantageous and preferred to administer these prodrugs orally, those prodrugs which exhibit enhanced oral bioavailability would offer a therapeutic advantage. Accordingly, prodrugs where one or more of $X_1$, $X_2$ and $X_3$ comprises a short chain hydrocarbylcarbonyl group are preferred. In view of their enhanced bioavailability when given orally in either a liquid or solid (e.g., capsule) form, particularly preferred are those prodrugs where $X_1$ is isobutyryl or pivaloyl and $X_2$ and $X_3$ are both hydrogen (compounds 10 and 11 of Table I) and where $X_1$, $X_2$ and $X_3$ are acetyl (compound C1 of Table I). Also preferred are those prodrugs where $X_1$ is n-butyryl and $X_2$ and $X_3$ are both hydrogen, and where $X_1$ and $X_3$ are both acetyl and $X_2$ is hydrogen. Especially preferred are certain prodrug compounds which have been isolated in an advantageous crystalline form, in particular 2',3',5'-triacetyl AICA riboside (Compound C1 of Table I), 3',5'-diacetyl AICA riboside (Compound 22 of Table I) and 3'-neopentoxycarbonyl (Compound 17 of Table I). Moreover, in the acetyl-substituted prodrug compounds, the leaving groups comprise acetate which is advantageously relatively pharmacologically silent.

Preferred Novel Prodrug Compounds

The preferred novel prodrug compounds of the present invention include those having the following formula:

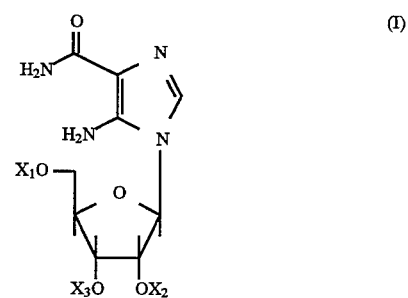

wherein $X_1$, $X_2$, and $X_3$ are independently (a) hydrogen, or (b)

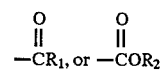

wherein $R_1$ is independently hydrocarbyl preferably of from 1 to about 24 carbon atoms or mono- or di-hydrocarbylamino, $R_2$ is independently hydrocarbyl preferably of form 1 to about 24 carbon atoms or (c) two of $X_1$, $X_2$ and $X_3$ taken together form a cyclic carbonate group; with the proviso that not all of $X_1$, $X_2$ and $X_3$ are hydrogen, acetyl, propionyl or benzoyl, or if one of $X_1$, $X_2$ and $X_3$ is hydrogen, the other two are not both benzoyl, or if $X_2$ and $X_3$ are hydrogen, then $X_1$ is not acetyl. Preferred $R_1$ and $R_2$ groups include lower alkyl groups. One preferred class of lower alkyl groups are those having at least one secondary or tertiary carbon atom. Another preferred class of lower alkyl groups are those having up to about 6 carbon atoms and optionally having a secondary or tertiary carbon atom. Hydrocarbyl groups having more than 24 carbon atoms may be used and are considered to be within the scope of the present invention.

Preferred compounds include those having one or two ester groups. Especially preferred are compounds having an ester group at either the 3'- or 5'-position or both positions of the ribosyl ring.

One preferred class of compounds comprises carbonate esters. Particularly preferred carbonate esters include compounds wherein $X_1$ or $X_3$ is

especially preferred are such compounds where $X_2$ is hydrogen. One such preferred group of compounds are those having a 3'-carbonate ester group. Especially preferred carbonate ester compounds, include those where $X_1$ and $X_2$ are both hydrogen and $X_3$ is isobutoxycarbonyl (compound No. 1 of Table I) or neopentoxycarbonyl (Compound No. 17 of Table I). Other preferred 3'-substituted carbonate esters include compounds Nos. 4, 3, and 7 of Table I.

One particularly preferred class of prodrug compounds include compounds which have enhanced water solubility. Such compounds are believed to exhibit enhanced bioavailability when given orally due to improved absorption from the gastrointestinal tract. For this reason, it is believed that prodrug compounds having one or two acyl ester groups are particularly advantageous. Especially preferred are short chain ester groups having less than about 6 carbon atoms. In particular, we have found compounds having an acyl ester at the 5' position or both the 3' and 5' positions of the ribosyl ring to be preferred. In particular, we have found compounds No. 10 (where $X_1$ is isobutyryl and $X_2$ and $X_3$ are both hydrogen), and No. 11 (where $X_1$ is pivalyl and $X_2$ and $X_3$ are both hydrogen) of Table I to be particularly preferred. Other preferred compounds include No. 31 (where $X_1$ is n-butyryl and $X_2$ and $X_3$ are both hydrogen) and No. 22 (where $X_2$ is hydrogen and $X_1$ and $X_3$ are both acetyl) of Table I. Especially preferred are 3'-neopentoxycarbonyl-AICA riboside (Compound 17 of Table I), 3',5'-diacetyl-AICA riboside (Compound No. 22) which have been isolated in an advantageous crystalline form; and, with respect to 3',5'-diacetyl AICA riboside, its 3'- and 5'-leaving groups comprise acetate (which is relatively pharmacologically silent).

Preparation of Preferred Compounds

The preferred carbonate ester and acyl ester compounds of the present invention may be conveniently prepared according to the following reaction scheme:

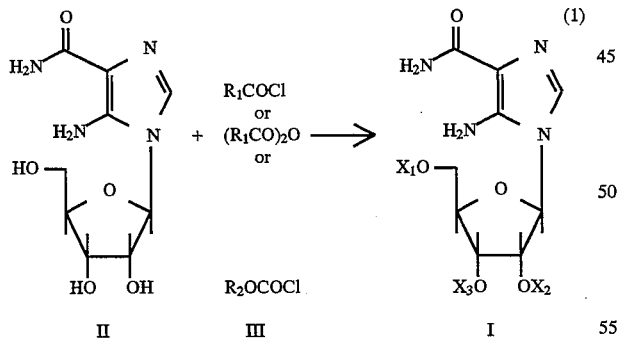

wherein $X_1$, $X_2$, $X_3$, $R_1$, and $R_2$, are as defined in conjunction with formula (I).

Reaction (1) is carried out by combining II, AICA riboside, and III, the appropriate acid chloride, acid anhydride or chloroformate, in solvents. The acid chloride may be conveniently prepared by conventional procedures such as reaction of the corresponding acid with thionyl chloride.

Some acid chlorides and acid anhydrides are commercially available. Many chloroformates are commercially available; also, the chloroformates may be conveniently prepared by conventional procedures known to those skilled in the art by the reaction of phosgene with the appropriate alcohol. Reaction (1) is conducted at a temperature of from about $-10°$ C. to about $5°$ C., preferably from about $-5°$ C. to about $0°$ C. and is generally complete within about 2 to about 4 hours. For ease of handling, the reaction is carried out in solvents. Suitable solvents include dimethylformamide (DMF), pyridine, methylene chloride and the like. For convenience, the reaction is carried out at ambient pressure. The reaction product(s) are isolated by conventional procedures such as column chromatography, crystallization and the like. As may be appreciated, the reaction may result in a mixture of products, mono, di, and tri-esters at the 2'-, 3'- and/or 5'-positions of the ribosyl moiety. The product esters may be separated by conventional procedures such as thin layer chromatography (TLC), high pressure liquid chromatography (HPLC), column chromatography, crystallization, and the like which are well known to those skilled in the art.

The 5'-monoesters may be conveniently prepared according to the following reaction scheme to give an intermediate blocked at the 2' and 3' positions:

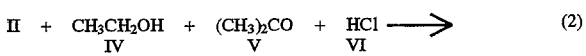

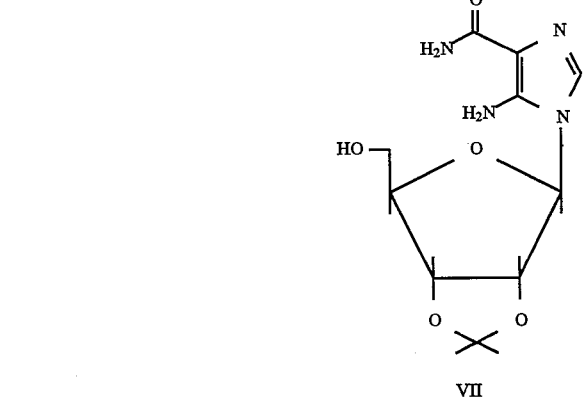

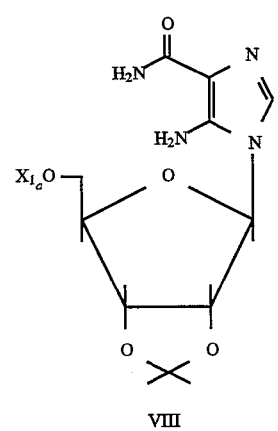

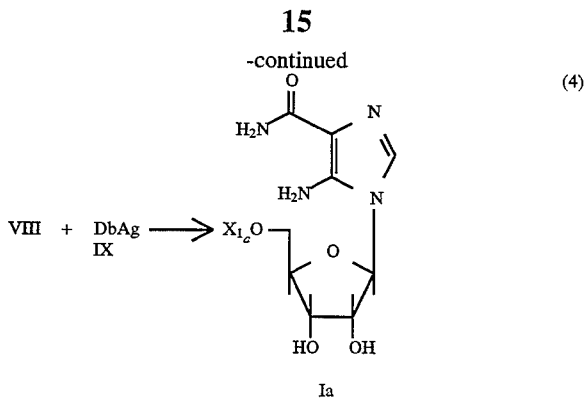

wherein $X_{1a}$ is

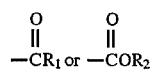

and DbAg is a deblocking agent.

Reaction (2) is conducted by combining II, IV, V and VI. Although the reactants may be combined in any order, it may be preferred to add II to a mixture of IV, V and VI. The reaction is carried out at a temperature of about 10° C. to about 25° C., preferably from about 15° C. to about 25° C. and is generally complete within about 45 minutes. Intermediate VI is isolated by conventional procedures.

Reaction (3) is the reaction of intermediate VII with the appropriate acid chloride, acid anhydride or chloroformate and is carried out as described in connection with Reaction (1).

Reaction (4) is an optional step to remove, if desired, the cyclic blocking group from the 2' and 3' positions. It is carried out by reacting with IX, the appropriate deblocking agent. Suitable deblocking agents include $H^+$ resin in water/acetone, tetraethyl-ammonium fluoride/THF, acetic acid/water, formic acid/water and the like. Such deblocking reactions are conventional and well known to those skilled in the art.

Mixed ester compounds may be conveniently prepared by first reacting AICA riboside with the appropriate acid chloride or acid anhydride according to Reaction (1) to add the acyl ester group and then reacting the acyl ester-substituted compound with the appropriate chloroformate according to Reaction (1) to obtain the mixed ester. Alternatively, mixed ester compounds may be prepared by first converting AICA riboside to a monoacyl ester according to Reaction (1) or Reaction (2) and then reacting the purified monoacylated product with the appropriate chloroformate according to Reaction (1). In addition, some mixed esters are prepared by first converting AICA riboside to a mono-alkoxy-carbonate according to Reaction (1) or (2) and then reacting the purified carbonate ester with an appropriate acid chloride or acid anhydride according to Reaction (1).

Carbocyclic AICA Riboside Compounds

We have discovered that carbocyclic AICA riboside has adenosine releasing agent properties. Thus, in another aspect, the present invention also provides a novel class of prodrugs of carbocyclic AICA riboside, and the use of carbocyclic AICA riboside and its prodrugs as adenosine releasing agents. These prodrugs are also useful as antiviral agents.

These prodrug compounds comprise a modified carbocyclic AICA riboside having a carbocyclic AICA ribosyl moiety which comprises an AICA moiety and a cyclopentyl moiety (where a carbon has replaced the oxygen in the ribosyl ring), and at least one hydrocarbyloxycarbonyl or hydrocarbylcarbonyl moiety per equivalent weight of carbocyclic AICA ribosyl moiety.

The carbocyclic AICA riboside and its prodrug compounds are useful in treating a variety of clinical conditions where increasing extracellular levels and release of adenosine would be beneficial. This invention is also directed to pharmaceutical compositions comprising an effective amount of carbocyclic AICA riboside or a prodrug compound thereof in a pharmaceutically acceptable carrier.

These carbocyclic AICA riboside prodrugs may be conveniently prepared by methods similar to those used in the preparation of the AICA riboside prodrugs described herein, substituting carbocyclic AICA riboside for AICA riboside as a starting material.

Utility

As noted previously, the prodrug compounds of the present invention are useful in treating a variety of clinical conditions where increased extracellular levels (and/or release) of adenosine are beneficial.

In particular, these compounds are useful in stroke therapy, either by prophylactic treatment or by treatment soon after the cerebral vascular event. These compounds are useful in mitigating the effects of other post-ischemic syndromes in the central nervous system, including the brain and spinal chord.

It is now clear that relatively short periods of brain ischemia set into motion a series of events that lead to an eventual death of selected neural populations in brain caused by the ischemia induced overproduction of the EAA neurotransmitters. Thrombolytic therapy of stroke is therefore not sufficient to protect against the ensuing neurologic damage after the occlusion is removed.

Since EAA's appear to be the major factor involved in post-stroke cell damage, blockade of EAA release in brain with adenosine might be beneficial in stroke therapy. Known glutamate receptor blockers have however been shown to lack specificity and produce many undesirable side effects, and the undesirable effects of adenosine administration have been noted. However, low doses of adenosine or an adenosine agonist with a high $A_1$ to $A_2$ affinity ratio or co-administration of a centrally acting agonist with an antagonist that cannot enter the central nervous system might avoid cardiovascular side effects and bind the $A_1$ receptors in the hippocampal regions thereby preventing or reducing EAA release.

AICA-riboside has been shown to protect against cellular degeneration that results after experimentally induced brain ischemia in two different animal model systems. The claimed prodrugs, by delivering AICA riboside should provide similar efficacy. In a gerbil model employing 5 minutes of global ischemia followed by reperfusion, AICA-riboside prevented the degeneration of hippocampal CA-1 cells, which in the control animals (non AICA-riboside treated) were virtually completely destroyed. Both intracerebroventricular (ICV) and IP administration of AICA riboside was effective in the gerbil model. In addition to the gerbil, two different rat models of focal ischemia were also used to evaluate AICA-riboside. One model employed partial reperfusion and the second total reperfusion. Both protocols showed a highly significant reduction in infarct size when a 800 mg/kg dose of AICA-riboside was given IP.

These compounds are also useful in treating other ischemic conditions, particularly those involving myocardial ischemia such as heart attacks and angina pectoris.

During a heart attack, adenosine is normally released and assists in maintaining the patency of ischemic vessels through vasodilation and inhibition of granulocyte free radical production and concomitant microvascular plugging, as described below. The prodrug compounds of the present invention enhance adenosine release and, therefore enhance the normal protective effect of adenosine during such an ischemic event. Adenosine levels are not altered significantly throughout the patient because alterations of adenosine production only occur in areas of, and at the time of, net ATP use and because adenosine is rapidly degraded. Thus, there will be a localized increased level of extracellular adenosine instead of a systemic or generalized adenosine enhancement.

Since many of the damaging events during ischemia occur rapidly, the prodrugs of the present invention should be present at the earliest possible moment. Accordingly, prophylactic use of these prodrugs may slow or interrupt the damaging process early enough to prevent any permanent damage. For example, the increased microvascular blood flow from vasodilation and decreased white cell sticking could maintain microvascular patency as well as in a sense wash away clots, clot promoting matter, or other deleterious agents from the proximal atherosclerotic regions.

In addition, since the prodrugs of the present invention when taken prophylactically would enhance adenosine release during an ischemic event, a heart attack patient undergoing such treatment would have a greater chance of not dying of a sudden arrhythmia before entry to the hospital. Such a prophylactic therapeutic regimen would protect the microvascular system and allow a longer time frame in which to institute thrombolytic therapy.

Moreover, the prodrugs of the present invention will also be useful in combination with thrombolytic agents such tissue plasminogen activator, streptokinase, and the like and also with other agents which are either free radical scavengers or agents which prevent the production of free radicals.

The prodrugs of the present invention are useful in treating reduced blood flow caused by myocardial arrhythmia. Prophylactic treatment with AICA riboside has been shown to result in decreased numbers of premature ventricular depolarizations and ventricular tachycardia episodes in animals and, more recently, decreased fatal ventricular fibrillation.

In addition, the prodrugs of the present invention may be useful in treating other conditions in which administration of AICA riboside has been beneficial. These include conditions such as treatment of autoimmune and inflammatory diseases and neurodegenerative diseases, conditions potentially associated with chronically low adenosine (including autism, insomnia, cerebral palsy, schizophrenia and other neuropsychiatric conditions), conditions associated with hyperglycemia (including diabetes mellitus and/or resulting from total parenteral nutrition), allergic conditions (especially by preventing the release of pharmacologically active substances by mast cells), and viral conditions, especially those associated with the human immunodeficiency disease.

However, as previously noted, AICA riboside is inefficiently absorbed from the gut and is poor in crossing the blood-brain barrier to penetrate the affected foci in the brain.

The advantageous features of more efficient absorption from the GI tract and better crossing of the blood brain barrier of the prodrug compounds of the present invention should give them increased efficacity and improved therapeutic effect as compared to AICA-riboside itself.

In addition the prodrug compounds of the present invention are useful as anticonvulsants and in preventing seizures in individuals with epilepsy including patients with homocysteineuria.

Both AICA riboside and some of these prodrug compounds have been shown to be active in preventing homocysteine-induced seizures in laboratory animals.

In addition AICA riboside and the prodrugs of the present invention should be efficacious in reducing ischemic injury to the CNS. The enhanced localized adenosine should cause local vasodilation, decreased granulocyte activation and trapping, and decreased glutamate release and excitatory neurotoxicity. The mild hypoglycemia resulting from administration of these compounds is also protective.

Figure 6:
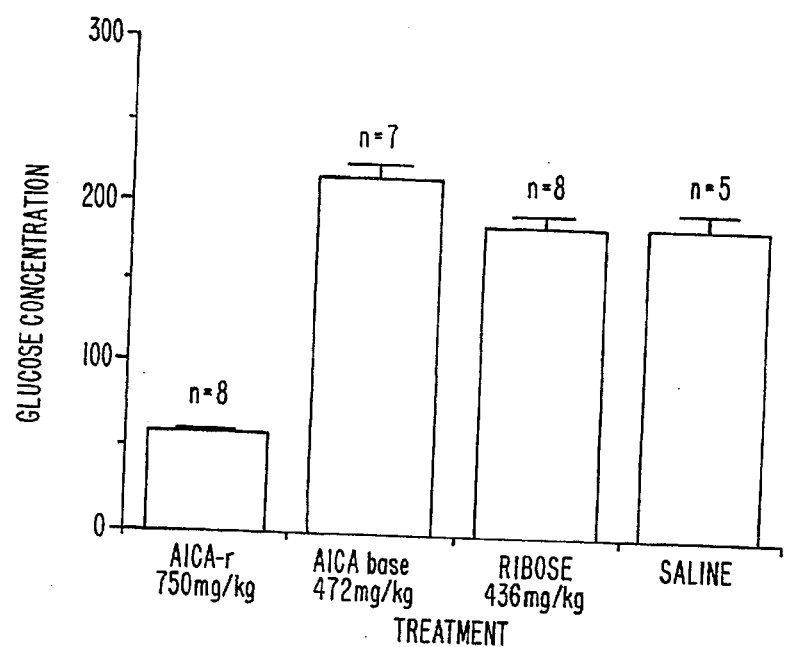
FIG. 6 depicts the activities of equimolar doses of ribose and AICA riboside in lowering blood glucose in fasted mice.

We have demonstrated that AICA riboside can cause hypoglycemia in rats, rabbits, dogs and man. This hypoglycemic effect may contribute to the anti-ischemic properties of the molecule. Ribose is known to lower blood glucose in several animal species, including man, in relatively high doses (on the order of about 1000 mg/kg) by an unknown mechanism, possibly by inhibition of phosphoglucomutase. Accordingly, in theory, AICA riboside could cause hypoglycemia at extremely high doses (approximately 3 gm/kg) due to its ability to deliver ribose phosphate to cells. Other means of increasing intracellular ribose such as treatment with ribose itself or other nucleosides and prodrugs and analogs of them which can be metabolized to yield ribose-1-phosphate (which is converted ribose-5-phosphate) or ribose-5-phosphate may also lower blood sugar. Surprisingly, we have found AICA riboside to lower blood glucose in rabbits at doses an order of magnitude lower than those effective for ribose, as low as about 200 mg/kg (see Table VI). At higher doses of AICA riboside, hypoglycemic seizures and death were induced in rabbits and mice. We have found rats to also be sensitive to the hypoglycemic effects of AICA riboside. Initial studies were performed using non-fasted rats (Sprague Dawley) and mice (Swiss-Webster). Decreases in plasma glucose levels ranging from 30–40% were seen with a dose of 750 mg/Kg in rats at 1 hour after administration. In non-fasted mice the decrease of glucose levels at this dose was greater, on the order of 30–50%. In both cases the hypoglycemia was statistically significant at the $p<0.01$ level. Fasted rodents have been shown to be more sensitive to the hypoglycemic effects of AICA riboside than fed rodents (See FIG. 7). Fasting the animals for 2–16 hours before drug administration significantly increased the hypoglycemic effect of AICA riboside. In fasted mice, AICA riboside is potent in lowering blood glucose. (See e.g., FIG. 6). In fasted mice AICA riboside may cause seizures at doses of 500 mg/Kg and above. In fasted mice (2 hours) a dose of 500 mg/Kg of AICA riboside reduced plasma glucose levels for 2–3 hours. In fasted mice (16 hours) a dose of 250 mg/Kg reduced glucose levels by 50% ($p<0.01$) and 60% at doses of 500 and 750 mg/Kg ($p<0.01$). Fasting therefore appears to potentiate the hypoglycemic effect of AICA riboside. To date, of the species tested, humans have been found to be the species most sensitive to the hypoglycemic effects of AICA riboside; doses of 25 mg/kg given intravenously over 30 minutes have caused significant reductions in serum glucose. (See FIG. 8). In rats made hyperglycemic by treatment with 50 mg/Kg streptozocin I.V, the hypoglycemic effect of AICA riboside was found to be more pronounced than in normal animals. Doses of AICA riboside as low as 100 mg/Kg I.P. resulted in marked decreases in plasma glucose that approached euglycemic levels. Thus, it appears that the potency of AICA riboside as a hypoglycemic agent may be potentiated in a diabetic state. We have also shown that tolerance to the chronic administration of AICA riboside does not develop.

Repeated administration of the drug for 6 days continues to yield a significant hypoglycemic response.

Figure 13A:
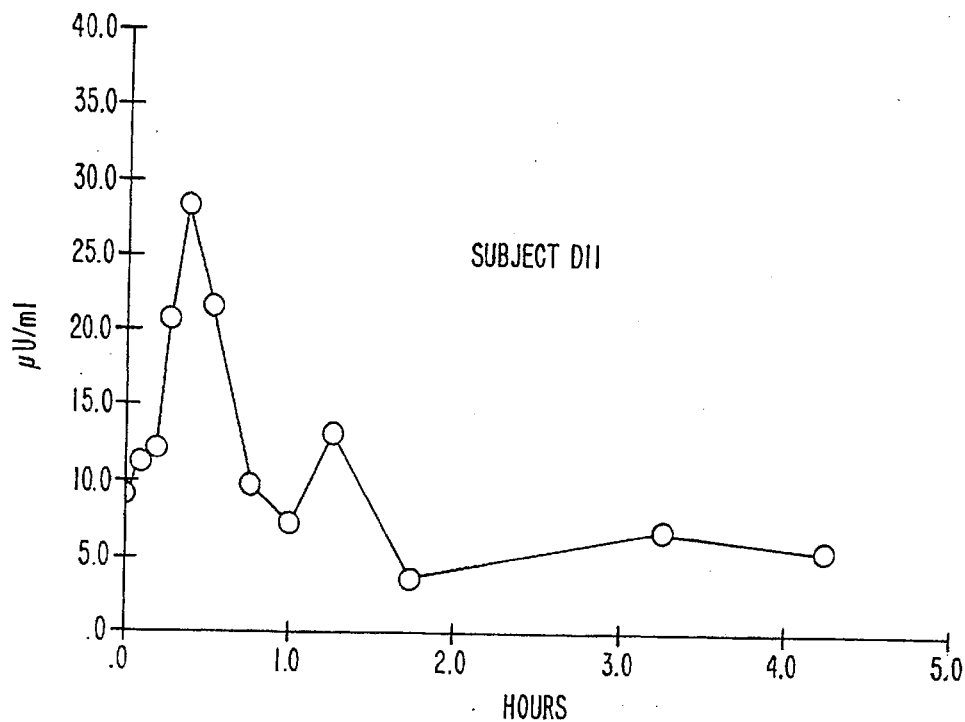
FIGS. 13A and 13B depict insulin levels in human plasma after administration of a 50 mg/kg dose of AICA riboside.
Figure 13B:
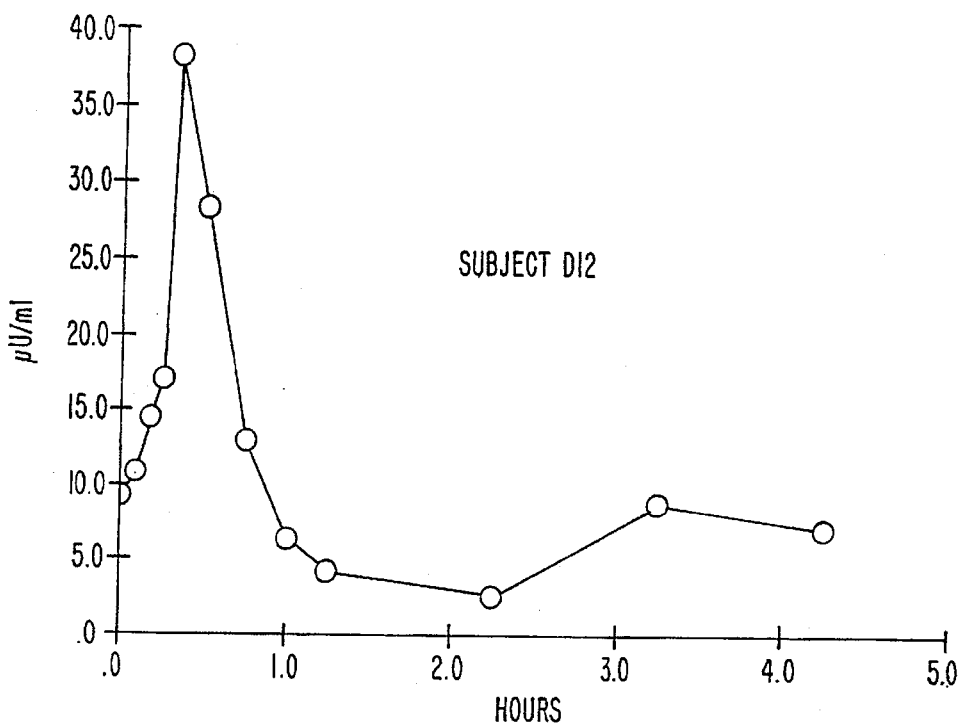

This leads to investigation of the mechanism of AICA riboside induced hypoglycemia. It appears that adenosine is not involved in the mechanisms of AICA riboside induced hypoglycemia, since adenosine and adenosine receptor agonists such as cyclohexyladenosine (CHA) and N-ethylcarboxamide adenosine (NECA) do not result in hypoglycemia but in fact produce a profound hyperglycemia (200–300% increases in plasma glucose, $p<0.01$) when administered I.P. in either rats or mice. This adenosine induced hyperglycemia is reversed by adenosine receptor antagonists (theophylline and sulphophenyltheophylline). Additionally, the AICA riboside-induced hypoglycemia is not blocked by theophylline. It is therefore concluded that the AICA riboside effect on plasma glucose is not mediated by adenosine. In rats, high doses of AICA riboside suppress blood insulin levels even at early time points after administration of the dose. However, human subjects exhibit significant elevations of serum insulin levels with administration of AICA riboside which precede the drop in blood glucose levels. (See FIG. 13).

Figure 11A:
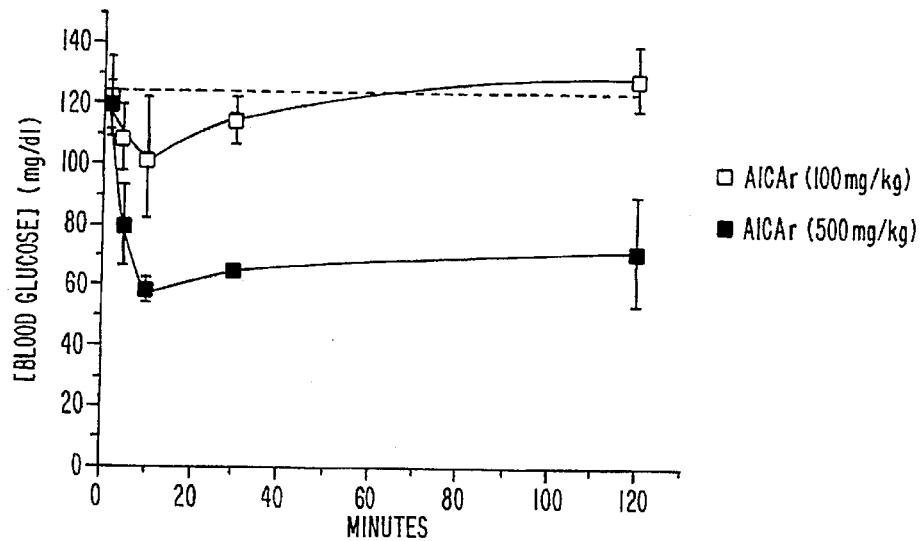
FIGS. 11A and 11B depict the effect of AICA riboside on blood glucose levels in conjunction with liver ZMP levels.
Figure 11B:
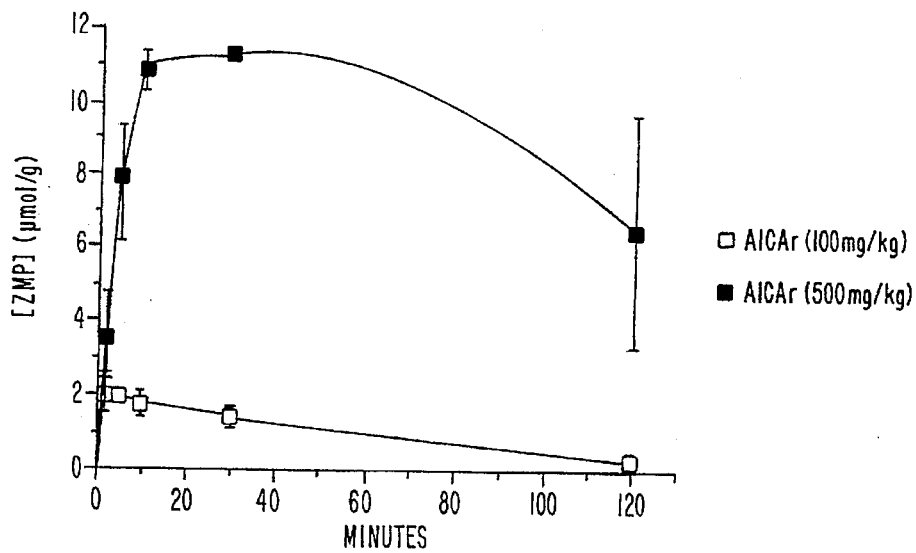
Figure 10A:
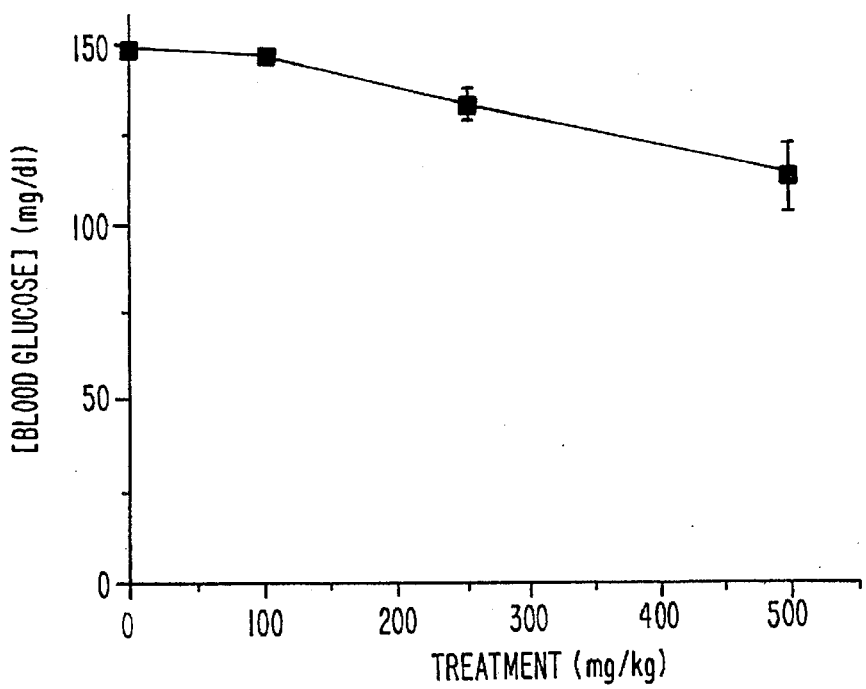
FIGS. 10A to 10D depict the effects of AICA riboside on serum lactate and pyruvate in rats.
Figure 10B:
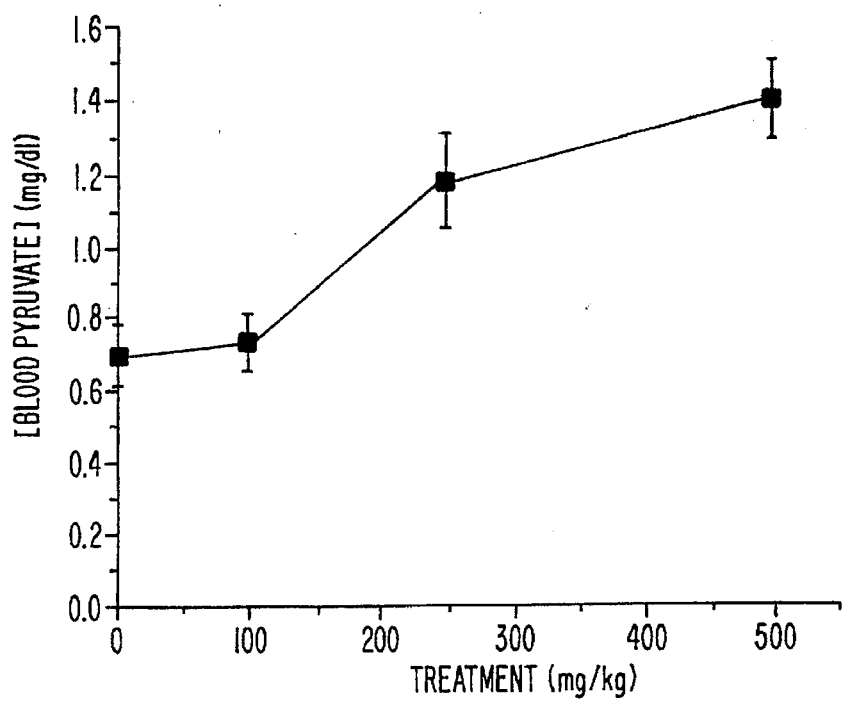
Figure 10C:
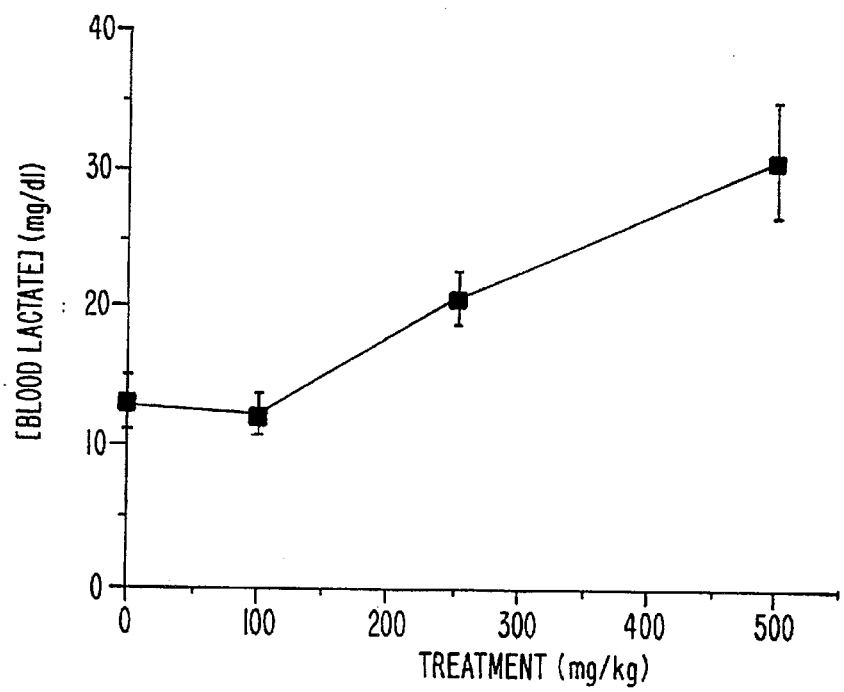
Figure 10D:
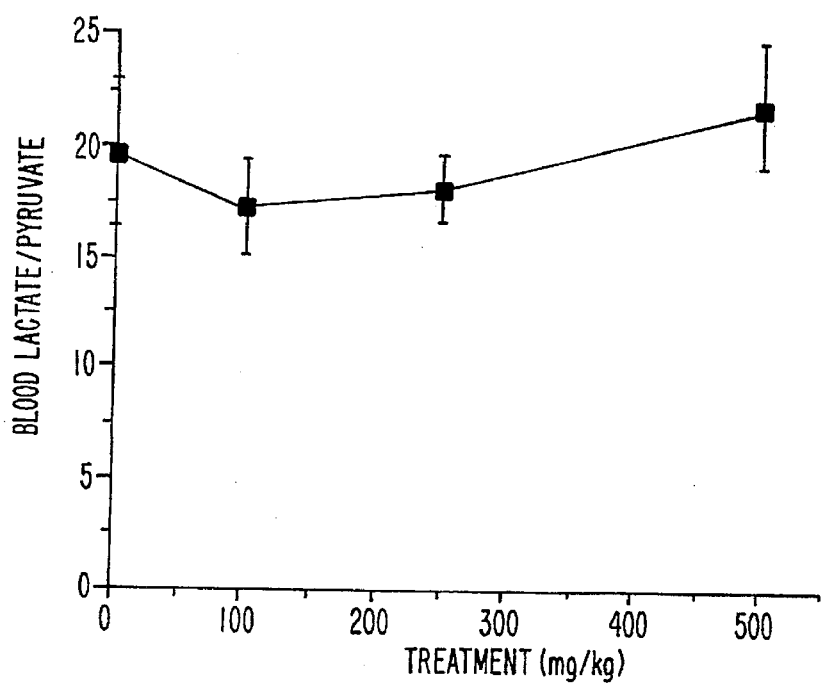
Figure 12:
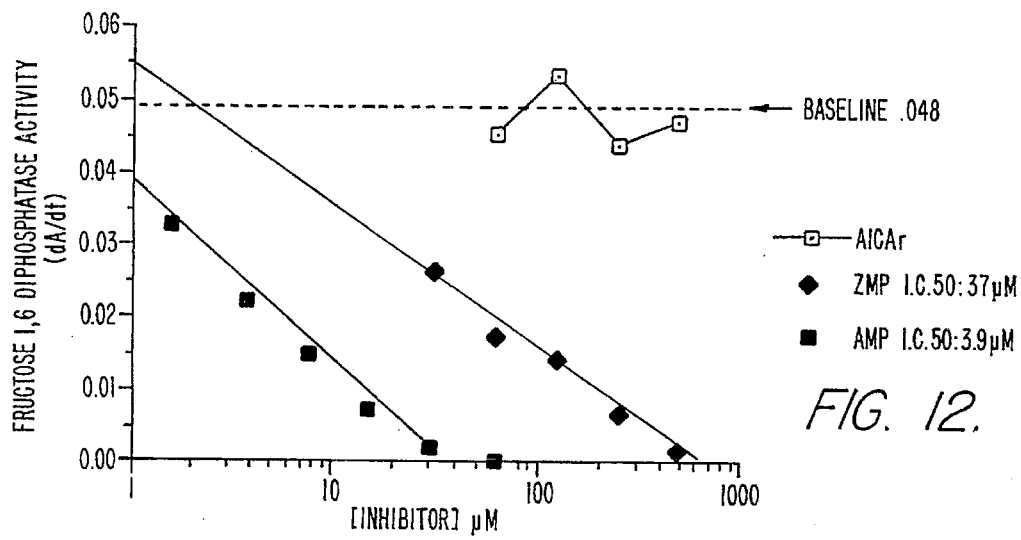
FIG. 12 depicts the activities of AICA riboside, ZMP and AMP in inhibiting fructose 1,6-diphosphatase in rabbit liver.

A dose of 750 mg/Kg in mice was shown to increase liver glycogen by 55% ($p<0.01$) suggesting that the drug inhibits liver glycogenolysis or activates glycogen synthesis and, thereby, contributes to the lowered plasma glucose levels. Rats exhibit an elevation of liver glycogen and of serum lactate and pyruvate; however, the lactate to pyruvate ratio is not changed. The lactate elevation suggests an interruption in gluconeogenesis, while the lack of change in the lactate to pyruvate ratio suggests no effect on mitochondrial function. (See FIGS. 9 and 10A to 10D). The glucose lowering effects of AICA riboside are related temporally to the generation and maintenance of liver ZMP levels in rats. (See FIGS. 11A and 11B). In studies employing rabbit liver, ZMP, but not AICA riboside, has been found to inhibit fructose diphosphatase ("FDPase") with a $K_I$ of about 40 µM (see FIG. 12).

Inhibition of pyruvate carboxylase, PEP carboxykinase or oxidative phosphorylation can interrupt mitochondrial function. However, AICA riboside does not interrupt mitochondrial function; the mild lactate build-up which occurs after administration of AICA riboside is not associated with a change in redox potential or a reduction in ATP pools. The mild lactate build up represents a minor interruption of the Cori cycle and should not, in itself, have detrimental effects. Doses of AICA riboside substantially higher than those causing elevation in lactate levels have been shown safe in toxicological studies.

Figure 16:
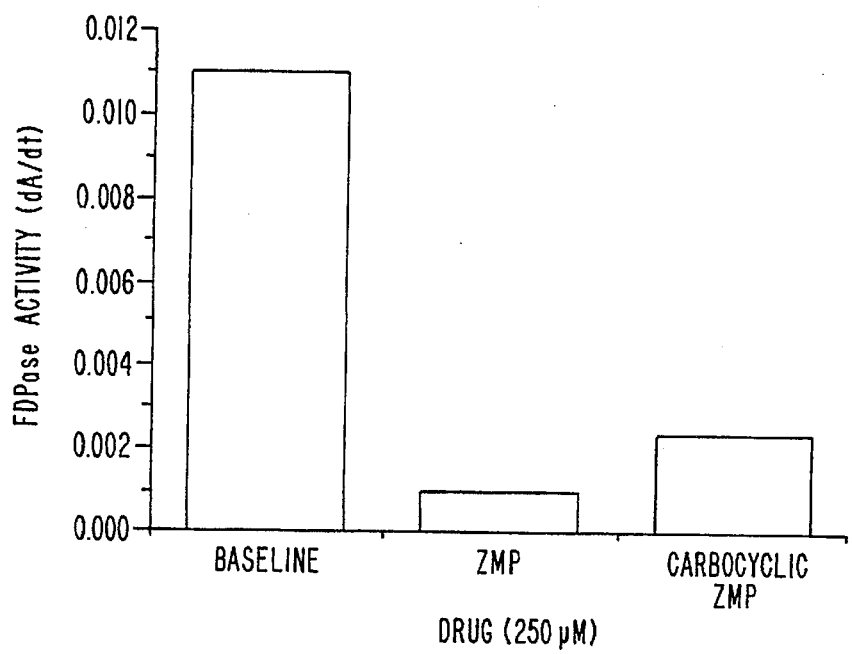
FIG. 16 depicts the effect of ZMP and carbocyclic ZMP as inhibitors of fructose 1,6-diphosphatase.

In vivo, AICA riboside may be phosphorylated by adenosine kinase to give AICA riboside-5'-monophosphate ("ZMP"). We believe that inhibition of fructose diphosphatase probably results from ZMP binding to the AMP inhibitory site of the enzyme. Thus, the enzyme falsely interprets a reduction in energy charge by the build-up in "false AMP", namely ZMP. ZMP can also cause an elevation of AMP levels (AMP is also an inhibitor of FDPase) via its inhibition of AMP deaminase. We have found that fructose diphosphatase may be inhibited using other ZMP analogs, including carbocyclic AICA riboside monophosphate. (See FIG. 16). Also useful are agents which cause or result in a build-up in ZMP (AICA ribotide). These agents include precursors in the de novo purine synthesis pathway or nucleosides, bases or prodrugs of such precursors. (See Lehninger, *Biochemistry*, p. 569 (1970)). Endogeneous ZMP levels may also be increased by agents which directly or indirectly inhibit AICA ribotide transformylase (thereby inhibiting folate metabolism), the enzyme which converts ZMP to 5'-formamido-imidazole-4-carboxamide ribonucleotide (precursor to inosinic acid). Accordingly, blood glucose levels may be decreased by administering agents which increase ZMP, either by increasing its synthesis or decreasing its conversion by AICA ribotide transformylase. Increased ZMP levels result in decreased FDPase activity and thus lower blood glucose levels. Thus, concomitant administration of one of these prodrugs of AICA riboside with an inhibitor of AICA ribotide transformylase may give enhanced hypoglycemic effects. Administration of any of the de novo purine synthesis intermediates (after the first committed step for purine synthesis, or their nucleosides or bases or their prodrugs, may similarly result in lowered blood glucose levels as mediated by ZMP. In addition, we have shown that 5-amino-1-β-D-ribofuranosyl-1,2,3-triazole-4-carboxamide, a purine nucleoside analog of AICA riboside lowers blood glucose in mice. AMP deaminase inhibitors can also be used to raise AMP concentration and inhibit FDPase, and thereby treat hyperglycemic conditions such as diabetes mellitis.

In summary, AICA riboside lowers blood glucose levels by at least three mechanisms. In man, AICA riboside causes (1) an early elevation of serum insulin levels, probably due to increased pancreatic release of insulin. AICA riboside administration causes (2) increased glycogen storage related to increased synthesis and/or decreased breakdown of glycogen. The glycogen storage effects of AICA riboside are probably only partially contributory to its hypoglycemic effects, since surprisingly, in glycogen depleted states such as prolonged fasting, profound hypoglycemia is induced more readily, i.e. at lower AICA riboside doses. Finally, AICA riboside appears to lower blood glucose (3) by inhibiting gluconeogenesis at the level of fructose diphosphatase; an ideal mechanism of therapy for type II diabetic patients who exhibit accelerated hepatic gluconeogluesis. Control of gluconeogenesis by inhibition of fructose diphosphatase is a preferred site of action in the gluconeogenesis pathway because fructose diphosphatase is specific for the synthesis of glucose; several other enzymes are used in both the synthesis and degradation pathways of glucose. Additionally, inhibition of fructose diphosphatase does not interfere with mitochondrial function. The combined effects from AICA riboside treatment, namely, increased insulin release, direct inhibition of gluconeogenesis and decreased glycogen utilization provide a profound, yet safe, reduction in blood glucose levels.

Figure 14:
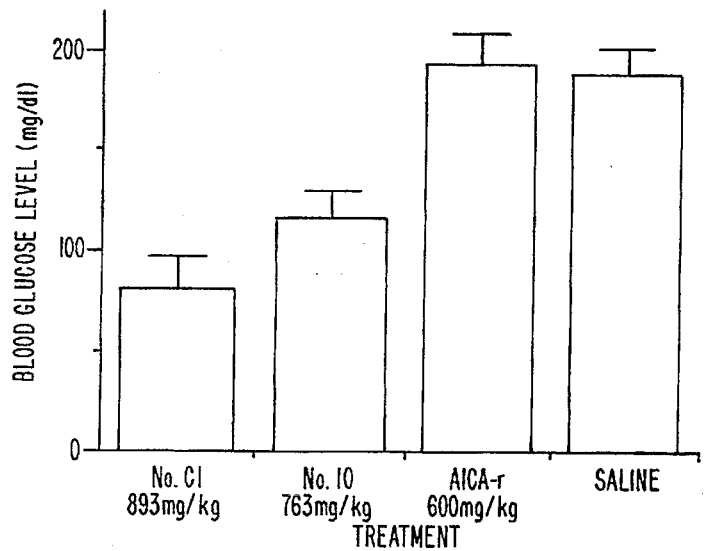
FIG. 14 depicts hypoglycemic effects of equimolar oral doses of some of the prodrugs of the present invention.

Due to the chronic nature of therapies for hypoglycemia and related diabetic conditions, and especially in the case of type II diabetic patients, therapeutic agents which may be administered orally are preferred. In another aspect of the present invention, we have found prodrugs of AICA riboside useful for increased delivery of the drug to the pancreas and liver after oral administration. Although AICA riboside itself is not well absorbed when given orally, administration of prodrugs of AICA riboside of the present invention, including acyl and carbonate esters, result in enhanced levels of serum AICA riboside and heart and liver ZMP. We have shown that oral administration of some of the AICA riboside prodrugs of the present invention produced hypoglycemia; whereas due to its low oral bioavailability, oral administration of AICA riboside, did not produce detectable hypoglycemia. (See FIG. 14)

As noted, the AICA riboside prodrugs of the present invention are useful in therapies for diabetes and related conditions. In addition, AICA riboside and these prodrugs are useful as a supplement to total parenteral nutrition as an agent to control hyperglycemia and/or hyperlipidemia.

Figure 17:
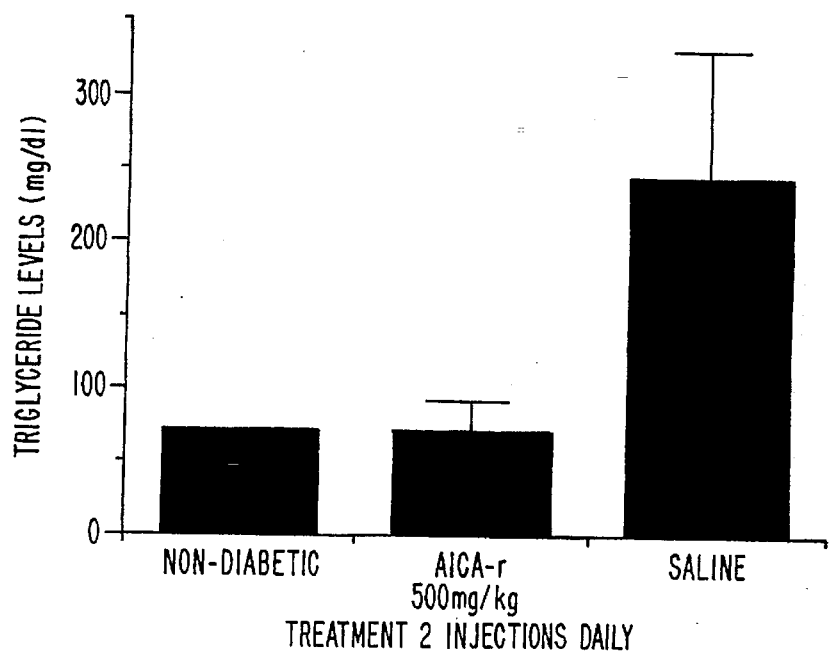
FIG. 17 depicts the effect of chronic AICA riboside administration on triglyceride levels in diabetic rats.

As noted previously we have found that adenosine releasing agents such as AICA riboside prevent or reduce (ischemic) injury associated with atherosclerosis. Since ischemic injury to heart, brain, eyes, kidneys, skin and nerves constitute significant long term complications associated with both type I and type II diabetes, the anti-ischemic properties of AICA riboside, its prodrugs and related analogs, will thereby confer added therapeutic benefits to diabetic patients. In addition, we have found that AICA riboside lowers serum triglycerides in streptozotocin-induced diabetes in rats. (See FIG. 17). Elevated triglycerides are associated with accelerated atherosclerosis and their normalization in those with diabetic conditions by the present invention should provide additional therapeutic utility in the treatment of diabetes.

S-AICA ribosyl homocysteine is formed from AICA riboside and homocysteine utilizing the enzyme S-adenosyl homocysteine hydrolase. This compound is a prodrug of AICA riboside. In addition, we have found AICA riboside is a weak inhibitor of adenosine kinase and that S-AICA riboside homocysteine is more potent. Inhibition of adenosine kinase by either AICA riboside or S-AICA ribosyl homocysteine can lead to increased adenosine release from cells undergoing net ATP catabolism.

During our study of these prodrugs we observed a surprising decrease in AMP concentrations in conjunction with no change in ATP concentration which would be caused by either an inhibition of adenosine kinase or an activation of AMP-5'-nucleotidase, or a combination of those effects. AMP 5'-nucleotidase is a highly regulated enzyme which has a regulatory protein which, when bound to the enzyme, inhibits its activity. AICA riboside or a metabolite thereof may activate AMP 5'-nucleotidase by preventing the binding of the regulatory protein to the enzyme.

Figure 15:
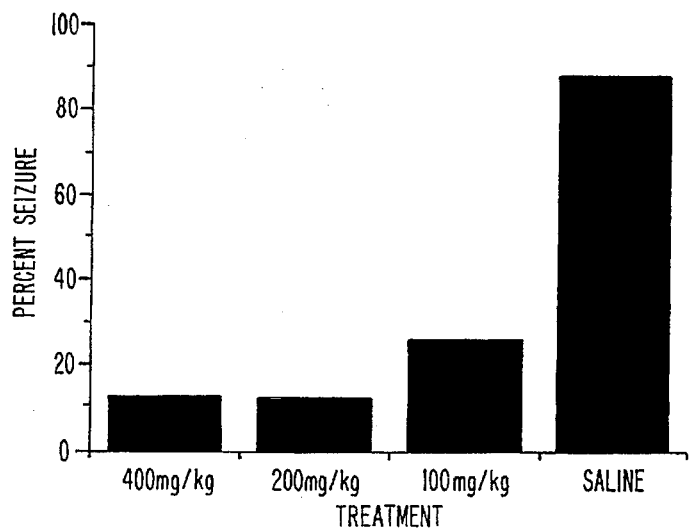
FIG. 15 depicts the effects of inhibition of adenosine kinase on the PTZ induced seizures.

This work on AICA riboside and its prodrugs has demonstrated that adenosine kinase is a potential site of action for the adenosine releasing agents. We have expanded this work on AICA riboside and S-AICA riboside homocysteine to examine other known adenosine kinase inhibitors as adenosine releasing agents. The flux (substrate made into product per unit of time), through adenosine kinase under physiological conditions is low; substrate metabolism is low partly due to low substrate availability. However, during net ATP catabolism, substrate availability (i.e. adenosine concentration) dramatically increases. In cell culture and in the rat heart ischemia models, we have found that inhibition of adenosine kinase by 5-iodotubercidin or by 5'-amino-5'-deoxyadenosine resulted in increased adenosine concentrations during net ATP breakdown. When 5'-amino-5'deoxyadenosine was administered to rats, it did not produce any significant changes in blood pressure or heart rate (i.e. no adenosine-mediated effects), yet in mice it was observed to prevent HTL-induced seizure, with the antiseizure effect being blocked by coadministration of the centrally acting adenosine antagonist theophylline. 5'-Amino-5'deoxyadenosine was also effective in blocking pentylenetetrazole (PTZ) induced seizures. (See FIG. 15).

Furthermore, AICA riboside has now been shown to be generated from ZMP during ischemia. The localized dephosphorylation of ZMP in a region of net ATP catabolism results in selectively high concentrations of AICA riboside and, therefore, ischemic selective effects of the molecule. For example, adenosine kinase and adenosine deaminase (ADA) would be only slightly inhibited by a dose of up to 500 mg/kg AICA riboside, but during tissue ischemia, the localized build-up of AICA riboside should cause increased inhibition of adenosine kinase and ADA. This ischemia-specific effect would avoid the deleterious effects of systemic ADA inhibition.

As noted, these AICA riboside prodrugs are useful as antiviral agents. They may be used to treat viral infections such as that caused by HIV. These prodrugs may also be used in combination with other antiviral agents, and when used in combination, may result in enhanced antiviral activity allowing lower doses and, thus, potentially decreased side effects resulting from those other antiviral agents.

Description of Preferred Embodiments

We have identified a series of prodrugs of AICA riboside having advantageous therapeutic properties. The structures of some of these prodrug compounds are depicted in Table I. Additional compounds proposed to be useful as prodrug are depicted in Tables II and III. These prodrug compounds should improve penetration of the blood-brain barrier in comparison with AICA riboside itself because of their longer plasma half-life.

A prodrug of AICA riboside with the assigned structure: 3'-isobutoxycarbonyl-AICA riboside which appears as Compound 1 of Table 1 ("5-amino-3'-(2-methyl-1-propoxycarbonyl)-1-β-D-ribofuranosyl-imidazole-4-carboxamide" or "Prodrug A") has been found to be particularly good for prolonging the half-life of AICA riboside and in penetrating the gut barrier. It has improved anticonvulsant activity against HTL-induced seizures when compared to AICA riboside. (FIG. 1).

Figure 2:
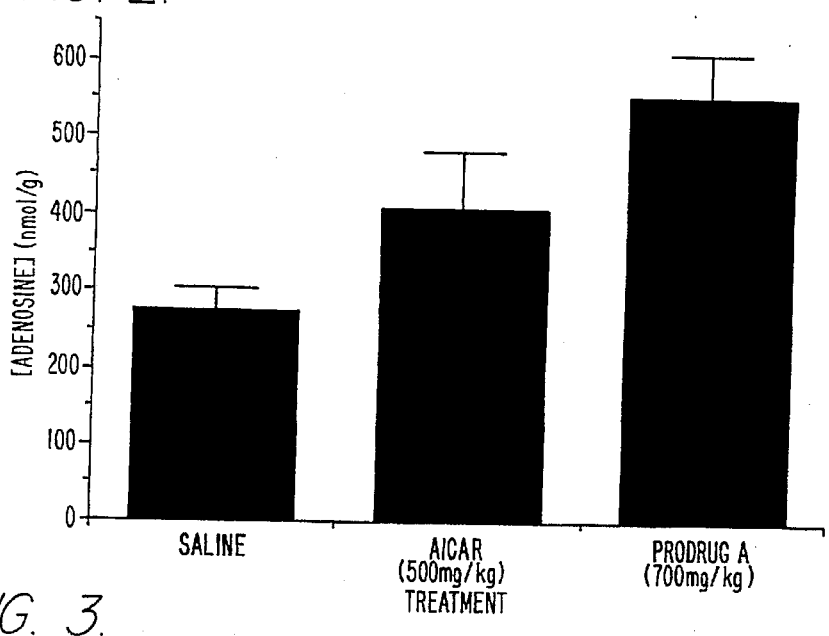
FIG. 2 depicts the activities of AICA riboside and Prodrug A in inducing adenosine production in ischemic rat heart tissue.

The ability of this compound to enhance adenosine production in an ischemic heart model has also been demonstrated (FIG. 2). Prodrug A was about 30% more potent on a molar basis than AICA riboside. The detection of substantial phosphorylated derivative of AICA riboside (ZMP) following administration of this compound further demonstrated that Prodrug A was in fact being cleaved to AICA riboside because that cleavage is necessary for the intracellular phosphorylation of AICA riboside to ZMP to occur. Surprisingly, Prodrug A also led to less AICA riboside and, therefore, less ZMP accumulation in the heart than an equimolar dose of AICA riboside and yet had more adenosine production indicating it may have intrinsic (analog) activity.

To further evaluate the intrinsic activity of Prodrug A, we have synthesized and tested a series of 3'-hydrocarbyloxycarbonyl derivatives of AICA riboside. As seen in FIG. 19, with an increasing number of carbon atoms in the side chain of the 3'-carbonate ester group, there is increased potency until four carbons are reached. Compounds having side chains in the carbonate ester of more than 4 carbon atoms (i.e. 5 and above) exhibited decreased activity in this experiment. We believe that these studies demonstrate the important and specific nature of this portion of the molecule for adenosine releasing activity.

In summary, 3'-isobutoxycarbonyl-AICA riboside has demonstrated improved enhancement of adenosine production as compared with the AICA riboside itself. It has an increased half-life as evidenced by the fact that it is cleared and phosphorylated more slowly than AICA riboside. Also, the maximum therapeutic effect of the compound appears to be greater than AICA riboside on a molar basis. This compound, furthermore, exhibits anti-seizure activity in the homocysteine-induced seizure model and increases adenosine production in the myocardial ischemia model. This compound also crosses the gut better than AICA riboside, as there is 5 times more ZMP accumulation in the liver after an equimolar gavage.

To assist in understanding the present invention, the following examples follow, which include the results of a series of experiments. The following examples relating to this invention are illustrative and should not, of course, be construed as specifically limiting the invention. Moreover, such variations of the invention, now known or later developed, which would be within the preview of one skilled in the art are to be considered to fall within the scope of the present invention hereinafter claimed.

EXAMPLE 1

Preparation of Carbonate Esters of AICA Riboside

Carbonate esters of AICA riboside are prepared according to the following procedure:

A 70 mmol portion of AICA riboside is suspended in a mixture of 50/ml N, N-dimethylformamide and 50/ml pyridine and then cooled in an ice-salt bath. To the resulting mixture the appropriate chloroformate (94 mmol, a 20 percent excess) is added under anhydrous conditions over a period of about 15 to 30 minutes with constant stirring. The ice salt bath is removed. The reaction mixture is allowed to warm to room temperature over about 1 to 2 hours. The progress of the reaction is monitored by TLC on silica gel, eluting with 6:1 methylene chloride:methanol, Disappearance of AICA riboside indicates completion of the reaction. The solvents are removed by evaporation under high vacuum (bath temperature less than 40° C.). The residue is chromatographed on a silica gel column packed with methylene chloride and is eluted initially with methylene chloride and then with methylene chloride: methanol 95:5. Fractions showing identical (TLC) patterns are pooled and then the eluate is evaporated to give a foam. The foam is dried overnight under high vacuum at room temperature.

The yield of the product carbonate esters is about 45 to 65%. Although the primary product is the 3'-carbonate ester, other product esters are formed.

EXAMPLE 2

Preparation of 3'-Isobutoxycarbonyl AICA Riboside

A solution of AICA riboside (18.06 g, 70 mmol) in a mixture of pyridine (50/ml) and N,N-dimethylformamide (50/ml) was cooled in an ice-salt mixture. To it was added an isobutyl chloroformate (11.47 g, 94 mmol) slowly over a period of 30 minutes with constant stirring. The initial red color of the reaction turned pale yellow in about 40 minutes. Stirring was continued for 2 hours at the end of which TLC on silica gel, eluting with methylene chloride: methanol 9:1 (Rf=0.3), indicated completion of the reaction. Methanol (2 ml) was added to neutralize unreacted reagents. The solvents from the reaction mixture were removed by evaporation under high vacuum (bath temperature approximately 40° C.). The sticky mass remaining was chromatographed over a silica gel column packed in a 9:1 methylene chloride: methanol mixture. The column was eluted with the same mixture and several fractions were collected. Fractions showing identical TLC spots were pooled and evaporated to obtain an off-white foam. The product isolated from the foam had the assigned structure, based on the nmr spectrum: 3'-isobutyloxycarbonyl-AICA riboside. Yield 8.5/g; mp 71°–73° (not a sharp mp).

IR (nujol): 1725 cm$^{-1}$ (—OCO$_2$CH$_2$CH(CH$_3$)$_2$). NMR (DMSO-d$_6$), δ ppm; 0.9 [d, 6H (CH$_3$)$_2$], 1.9 (m, 1H, CH of isobutyl side chain), 3.6 (m, 2H, 5'-CH$_2$), 3.9 (d, 2H, CH$_2$ of isobutyl side chain), 4.1(m, 1H, 4'-CH), 4.6(1, 1H, 2'-CH), 5.01(dd, 1H, 3'-CH), 5.45–5.55(m, 2H, 1'-CH and 5'-OH), 5.92(d, 1H, 2'-OH), 6.02(br.s, 2H, 5-NH$_2$), 6.6–6.9(br. d, 2H, 4-CONH$_2$), 7.35 (S, 1H, 2-CH).

The spectra of this compound was compared with that of its parent compound, AICA riboside and showed that 3-CH (which appears at 4.05 ppm in AICA riboside), had shifted down field by 1 ppm due to a substitution on the oxygen attached to the same carbon atom, while the positions of all the other protons remained unchanged for the most part, thus confirming the substitution to be on 3'-C.

Although nmr of the product of Example 2 indicated that it was at least 80% of the 3'-isobutoxycarbonate ester (Compound 1 of Table I), HPLC analysis showed several peaks. The fractions corresponding to each peak were collected and analyzed on HPLC. Each peak also showed the presence of two major products, designated A and B. One of them (product A) was determined to be AICA riboside and the other (product B) was isolated in small quantities and characterized as AICA riboside-2', 3'-cyclic carbonate based on its nmr and mass spectral data. NMR(DMSO-d$_6$) δ ppm; 3.6–3.7(m, 2H, 5'-CH$_2$), 4.3 (g, 1H, 4'-CH), 5.35 (m, 1H, 3'-CH), 5.6 (m, 1H, 2'-CH), 5.2–6.7 (br, 1H, 5'-OH), 5.8–6.0 (br, 2H, 5-NH$_2$), 6.1 (d, 1H, 1'-CH), 6.7–6.95(br, d, 2H, 4-CONH$_2$), 7.45 (S, 1H, 2-CH). Mass spec. (FAB) M$^+$, 284; M$^{+1}$ 285, M$^{+2}$ 286. These data confirmed the structure of the compound (product B) to be 2'3'-cyclic carbonate of AICA riboside. A preferred method of synthesis of this compound is set forth in Example 3 below.

EXAMPLE 3

Preparation of AICA Riboside 2', 3'-Cyclic Carbonate

To a suspension of AICA-riboside (5.16/g, 20 mmol) in pyridine (50/ml), p-nitrophenyl chloroformate 92.5/g, 25 mmol) was added in one lot and stirred at room temperature for 5 days at the end of which TLC on silica gel, eluting with methylene chloride: methanol, (6:1 Rf=0.4), indicated completion of the reaction. Pyridine from the reaction mixture was removed by evaporation. The residue was chromatographed over a silica gel column, eluting with methylene chloride:methanol (9:1). The fractions which showed identical TLC were pooled and evaporated to obtain a foam (yield, 4.0 g). This product was identical to AICA riboside-2',3'-cyclic carbonate, isolated as one of the by-products from the synthesis described in Example 2 and characterized by nmr and mass spectral analysis.

EXAMPLE 3A

Preparation of AICA Riboside 2',3'-Cyclic Carbonate

In a 100 ml round bottom flask fitted with a vacuum adapter 5.0 g of 3'-isobutoxy carbonyl AICA-riboside was taken and immersed in a preheated oil bath (bath temperature 100°–110° C.) while vacuum was applied gradually. After about 45 minutes of heating under vacuum, the product was cooled and crystallized from hot methanol. The colorless crystalline product was collected by filtration and dried under vacuum. The product was found to be identical to AICA-riboside-2',3'-cyclic carbonate, isolated as one of the byproducts from an earlier procedure (Example 2) as characterized by TLC and other spectroscopic data comparison. Yield was 3.1 g of a solid melting point 66°–68° C.

EXAMPLE 4

Preparation of 5'-Acetyl AICA Riboside (A) Preparation of 2',3'-Isopropylidene AICA Riboside:

To a mixture of dry HCl gas (9.0 g) dissolved in dry acetone (115 ml) and absolute ethanol (138 ml), AICA-riboside (12.9 g), was added. The mixture was stirred at room temperature for two hours. Completion of the reaction was monitored by TLC. The reaction mixture was stirred an additional two hours at room temperature at which time TLC indicated that the reaction was complete. The reaction mixture was poured slowly into an ice-cold mixture of ammonium hydroxide (18 ml) and water (168 ml). The pH of the solution was adjusted to about 8 by adding a few ml of ammonium hydroxide. The reaction was concentrated to 100 ml. The ammonium chloride precipitate was removed by filtration. The filtrate was concentrated again to precipitate additional ammonium chloride. After filtering, the filtrate was evaporated to dryness. The residue was extracted three times with 200 ml aliquots of methylene chloride. Evaporation of methylene chloride gave a foam which was characterized by nmr spectroscopy to be the product 2',3'-isopropylidene AICA riboside which was used in the following reaction without further purification.

(B) To a solution of 2',3'-isopropylidene AICA riboside in 25 ml dry pyridine cooled in an ice-salt mixture, 10 ml acetic anhydride was added dropwise with stirring; the mixture was warmed to room temperature over a period of two hours. The reaction was shown to be complete by TLC (9:1 methylene chloride: methanol). The solvents were removed from the reaction mixture by evaporation. The residue was coevaporated twice with two 25 ml aliquots of N, N-dimethylformamide. That product was treated with 100 ml of 80% acetic acid for twenty-four hours. Completion of the reaction was indicated by TLC on silica gel eluting with 6:1 methylene chloride:methanol. Water and acetic acid were removed by evaporation under reduced pressure. The residue was coevaporated four times with 100 ml aliquots of water to remove the acetic acid. The residue was crystallized from 25 ml 1:1 ethanol:water. The crystalline product was collected by filtration, washed with water and dried under vacuum to give 3.0 g of the above-identified product, melting point 165°–166° C.

IR(nujol); 1745 cm$^{-1}$ (—OCOCH$_3$). NMR (DMSO-d$_6$), δ ppm: 2.0 (S,3H, COCH$_3$), 4.0–4.1 (m, 2H, 5'-CH$_2$), 4.1–4.4 (m, 3H, 2'-CH, 3'-CH, 4'-CH), 5.3 (d, 1H, 1'-CH), 5.4–5.6 (m, 2H, 3'-OH, 4'-OH), 5.7–5.9 (br, 2H, 5-NH$_2$), 6.6–7.0 (br. d, 2H, CONH$_2$), 7.3 (S, 1H, 2-CH).

EXAMPLE 4A

Preparation of 2',3'-Isopropylidene AICA Riboside

To a solution of 230 ml acetone, 275 ml ethanol and 58 ml of 9.5M HCl in ethanol, 26 g AICA riboside were added. The resulting mixture was stirred for 35 minutes. The reaction mixture was added to a solution of 500 ml ice and 75 ml ammonium hydroxide (14N). The solution was concentrated to 100 ml; then 300 ml n-butanol and 100 ml water were added. The organic phase was separated and washed with 50 ml water. The combined aqueous phases were extracted with 100 ml n-butanol. The combined organic (n-butanol) phases were concentrated to give a white foam. The foam was dissolved in 75 ml ethanol and left in the freezer. The crystalline product was collected by filtration, washed with ethanol and dried under vacuum to give 19.9 g of the above-identified product, melting point 184°–185° C. (literature: 185°–186° C.). Reference: Srivastava et al., J. Med. Chem. 18:1237 (1975).

EXAMPLE 5

Preparation of 5'-Alkoxycarbonyl-AICA Riboside Derivatives

Four different 5'-alkoxycarbonyl-AICA riboside derivatives were made according to the following general procedure using the appropriate starting materials:

To an ice-cold solution of 10 mmol 2',3'-isopropylidene-AICA riboside in 40 ml pyridine, a solution of 15 mmol of the appropriate alkylchloroformate in 10 ml methylene chloride was added over a period of about 15 minutes. The cooling bath was removed and the reaction mixture was stirred for about four hours. At the end of that time period, thin layer chromatography (TLC) with silica gel, eluting with methylene chloride:methanol 9:1, indicated that the reaction was complete. The solvent was removed by evaporation under high vacuum. The residue was coevaporated with DMF (2×20 ml). The product was dissolved in about 100 ml methylene chloride and extracted with water (2×100 ml). The organic layer was dried over sodium sulfate and evaporated to obtain a syrup-like product which was carried into the following step for deblocking of isopropylidene group.

The above product was dissolved in 60 ml of 50% formic acid and then heated at 65° C. for two hours. At the end of that time, TLC on silica gel eluting with methylene chloride: methanol 6:1, indicated that the reaction was complete. Water and formic acid were removed by evaporation under high vacuum. The residue was co-evaporated with water (2×25 ml) and ethanol (2×25 ml). The product was chromatographed over a silica gel column, eluting with methylene chloride: methanol, 9:1. Effluents containing fast-moving products were rejected. Effluents containing the major product were pooled and evaporated to obtain a glassy product which was dried under high vacuum. The yields of each of the products made according to this procedure and their physical data are summarized below.

A. 5'-Ethoxycarbonyl AICA-Riboside

Yield about 35%.

IR (KBr) cm$^{-1}$: 3000–4000 (broad peaks, OH, NH$_2$, CONH$_2$), 1730 (0-C00-Et), 1660 (CONH$_2$)

$^1$H-NMR(DMSO-d$_6$) δppm: 1.2(t, 3H, CH$_3$ of ethyl), 3.9–4.1 (m, 2H, 5'-CH$_2$), 4.1–4.25 (q, 2H, —OCH$_2$ of ethyl side chain), 4.25–4.4 (m, 3H, 2'-CH, 3'-CH, and 4'-CH), 5.45 (d, 1H, 1'-CH), 5.45–5.6 (2d, 2H, 2'-OH and 3'-OH), 5.8–9.0 (br.5, 2H, 5-NH$_2$), 6.6–6.9 (br.d, 2H, CONH$_2$), and 7.25 (S, 1H, 2-CH).

5'-Isobutoxycarbonyl-AICA Riboside

Yield 40%

IR(KBr) cm$^{-1}$: 3000–4000 cm$^{-1}$ (broad peaks, OH, NH$_2$, CONH$_2$, etc. )

$^1$H-NMR (DMSO-d$_6$), δppm, 0.8–0.9 (d, 6H, 2CH$_3$ of isobutyl side chain), 1.8–2.0 (m, 1H, CH of isobutyl side chain), 3.8–3.9 (d, 2H, CH$_2$ of isobutyl side chain), 4.0–4.1 (m, 2H, 5'-CH$_2$), 4.1–4.4 (m, 3H, 2'-CH, 3'-CH, and 4'-CH), 5.4 (d, 1H, 1'-CH), 5.5–5.1 (2d, 2H, 2'-OH and 3'-OH), 5.8–5.9 (br.s, 2H, 5-NH$_2$), 6.6–6.9 (br.d, 2H, COHN$_2$) and 7.25 (5, 1H, 2-CH).

C. 5-Neopentoxycarbonyl-AICA-Riboside:

Yield: 35%

$^1$H-NMR (DMSO-d$_6$), δppm: 0.8 (S, 9H, 3CH$_3$), 3.8 (5, 2H, -CH$_2$O—of neopentoxy side chain), 4.0–4.1 (m, 2H, 3'-CH and 4'-CH), 4.2–4.45 (m, 3H, 2'-CH and 5'-CH$_2$), 5.5 (d, 1H, 1'-CH), 5.3–5.7 (m, 2H, 2'-OH and 3'-OH), 5.8–5.9 (br.s, 2H, 5-NH$_2$), 6.6–7.0 (br.d, 2H, CONH$_2$), and 7.3 (5, 1H, 2-CH).

D. 5'-Cyclopentyloxycarbonyl-AICA-Riboside

Yield: 38%

$^1$H-NMR (DMSO-$d_6$), δppm: 1.3–2(br, m, 8H, 4 $CH_2$ groups of the cyclopentane ring), 3.9–4.2 (m, 2H, 3'-CH and 4'-CH), 4.2–4.4 (m, 3H, 2'-CH and 5'-CH), 4.9–5.1 (m, 1H, CH—O of cyclopentane ring), 5.4 (d, 1H, 1'-CH), 5.45–5.65 (2d, 2H, 2'-OH and 3'-OH), 5.9 (br.s, 2H, 5-$NH_2$), 6.6–6.9 (br.d, 2H, $CONH_2$), 7.3 (5H, 2'-CH).

EXAMPLE 6

Preparation of 2'3'5'-Tri-O-N-Butyryl-AICA-Riboside

This compound was prepared according to the method described by for the preparation of 2', 3', 5'-tri-o-acetyl-AICA-riboside. (Reference: Suzuki and Kumashiro, U.S. Pat. No. 3,450,693; Chem. Abstr. 71:81698Z (1969)).

The yield was 70% and the product had a melting point of 97°–100° C.

IR (KBr) $cm^{-1}$: 3200–3400 ($NH_2$, $CONH_2$), 1720–1745 ($OCOCH_2CH_2CH_3$), 1650 ($CONH_2$).

$^1$H-NMR (DMSO-$d_6$), δppm: 0.7–1.0 (m, 9H, $CH_3$), 1.3–1.7 (m, 6H, —$CH_2$—), 2.1–2.6 (m, 6H, —$COCH_2$—), 4.2 (br.s, 3H, 5'-$CH_2$ and 4'-CH), 5.3–5.4 (m, 1H, 3'-CH) 5.6 (t, 1H, 2'-CH), 5.9 (d, 1H, 1'-CH) 6.0 (bros, 2H, $NH_2$), 6.8 (br.d, 2H, $CONH_2$) 7.4 (S, 1H, 2-CH)

EXAMPLE 7

Preparation of 2',3',5'-Tri-O-Succinyl-AICA-Riboside

A mixture of 5.2 g AICA riboside and 12.0 g succinic anhydride dissolved in a mixture of 30 ml DMF and 30 ml pyridine was stirred at 40° C. for 18 hours and then evaporated to dryness under high vacuum. The residue was dissolved in water and applied to a 150 ml column of amberlite IRC-120 (H+). The column was washed with water and then eluted with 1N ammonium hydroxide. The eluate was evaporated to dryness under vacuum. The residue was dissolved in water and applied to a 30 ml column of Dowex-2 (formate). The column was washed with water and eluted with formic acid. The formic acid eluate was concentrated and then lyophilized to yield 0.55 g of the product (approximately 5% yield).

$^1$H NMR ($D_2O$), δppm: 2.4–2.8 (m, 12H, —$CH_2$—), 4.4 (m, 2H, 5'-$CH_2$), 4.6 (m, 1H, 4'-CH), 5.2 (m, 1H, 3'-CH), 5.4 (m, 1H, 2'-CH), 5.8 (d, 1H, 1'-CH), 7.9 (S, 1H, 2-CH).

EXAMPLE 8

Preparation of 3',5'-Diacetyl-AICA-Riboside

To a solution of 10.0 g 2',3',5'-tri-o-acetyl-AICA-riboside in 150 ml pyridine, 3.0 g hydroxylamine hydrochloride was added. The reaction mixture was stirred at room temperature; progress of the reaction was monitored using TLC (silica gel, methylene chloride: methanol 9:1) After three days of stirring, an additional 2.0 g of hydroxylamine hydrochloride was added. The reaction mixture was stirred for an additional three days. At the end of that time, 80% of the starting material had disappeared, according to TLC. Acetone (10 ml) was added to the reaction mixture to neutralize unreacted hydroxylamine hydrochloride; the resulting mixture was stirred for an additional five hours. Solvent was removed by evaporation under reduced pressure. The residue was coevaporated with N,N-dimethylformamide (DMF) (2×100 ml). The product obtained was chromatographed over a silica gel column which was packed in, and eluted with, a 9:1 mixture of methylene chloride: methanol. Fractions showing homogeneous spots at $R_f$=about 0.5 were pooled and then evaporated. The residue was crystallized from ethyl acetate to give a light pink crystalline product whose $H^1$-NMR indicated that it was a mixture 2',5'-diacetyl-AICA-riboside and 3',5'-diacetyl-AICA-riboside in a ratio of about 1:5. A second crystallization from ethyl acetate gave a product which was about 96% isomerically pure 3',5'-diacetyl-AICA-riboside, having a melting point of 132°–134° C. About 3.0 g of product was obtained (about 35% yield).

IR (KBr) $cm^{-1}$: 3200–3460 (broad peaks, OH, $NH_2$, $CONH_2$, etc.); 1760, 1740 (3'-$OCOCH_3$ and 5'-$OCOCH_3$), 1660 ($CONH_2$).

$^1$H-NMR (DMSO-$d_6$), δppm: 2.0–2.1 (2s, 6H, 3'-$OCOCH_3$ and 5'-$OCOCH_3$), 4.25 (br.s, 2H, 5'-$CH_2$), 4.6 (q, 1H, 2'-CH), 5.1 (m, 1H, 4'-CH), 5.5 (d, 1H, 2'-OH), 5.9 (m, 3H, 5-$NH_2$ and 1'-CH), 6.8 (br.d, 2H, —$CONH_2$), 7.35 (s, 1H, 2-CH).

EXAMPLE 9

Preparation of AICA-Riboside-5'-N,N-Diethylsuccinamate

To a solution of 2.98 g 2',3'-isopropylidene AICA riboside, 1.73 g N,N-diethylsuccinamic acid and 1.2 g 4-dimethylaminopyridine in 25 ml of DMF which was cooled in a dry ice-methanol bath, 2.26 g N,N-dicyclohexylcarbodiimide was added in one lot. The reaction mixture was stirred and allowed to warm to room temperature. The reaction was complete after about 18 hours, as evidenced by the disappearance of most of the starting material as determined by TLC. The by product cyclohexylurea that separated as a white solid was removed by filtration and then washed with DMF (2×10 ml). The filtrate and DMF washings were combined and then concentrated under high vacuum. The residue was chromatographed over a silica gel column, eluting with methylene chloride: methanol, 19:1. The fractions showing the major spot (TLC $R_f$-0.6) were pooled and evaporated to obtain a syrupy product which was taken to the following step to remove the isopropylidene blocking group.

The syrupy product was dissolved in 25 ml of a 60% formic acid solution. The resulting mixture was stirred at room temperature for 48 hours. At the end of that time TLC indicated hat the reaction was complete. The reaction mixture was concentrated under high vacuum to give a thick syrup. The syrupy residue was coevaporated with water (2×20 ml) and ethanol (2×25 ml). The product was crystallized from 25 ml ethanol:water (9:1) to give 900 mg of the above-identified compound, melting point 180°–181° C.

IR(KBr)$cm^{-1}$: 3000–4000 ($NH_2$, OH, etc.), 1725,

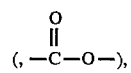

1610–1650 ( , $CONH_2$ and $CON(CH_2CH_3)_2$).

$^1$H-NMR (DMSO-$d_6$), δppm: 0.9–1.15 (2t, 6H, 2$CH_3$ of the two ethyl groups), 2.5 (m, 4H, —CO—$CH_2CH_2$—CO—), 3.1–3.4 (m, 4H, —$H_2$C—N—$CH_2$—), 4.0 (m, 2H, 5'-$CH_2$), 4.15–4.35 (m, 3H, 2'-CH, 3'-CH and 4'-CH), 5.35 (d, 1H, 1'-CH), 5.5 (2d, 2H, 2'-OH and 3'-OH) 5.8 (br, 2H, 5-$NH_2$), 6.6–6.9 (br.d, 2H, $CONH_2$), and 7.3 (s, 1H, 2-CH).

EXAMPLE 10

Preparation of 3'-Neopentoxy Carbonyl-AICA Riboside

The above-identified compound was prepared according to the procedure described in Example 2 for the preparation of 3'-isobutoxycarbonyl-AICA riboside, substituting neopentyl chloroformate for isobutylchloroformate. In this preparation, the product was crystallized from hot water to give 8.1 g (yield about 30%) of the above-identified compound as a crystalline solid, melting point 119°–121°C.

$^1$H-NMR (DMSO-d$_6$), δppm: 0.8–1 (m, 9H, 3CH$_3$ groups of the neopentyl side chain), 3.6 (m, 2H, 5'-CH$_2$), 3.8 (s, 2H, —CH$_2$O— of the neopentyl side chain), 4.1 (m, 1H, 2'-CH), 3.6 (q, 1H, 4'-CH), 5.05 (d, 1H, 3'-CH), 5.5 (m, 2H, 2'-OH and 5'-OH), 5.9 (d, 1H, 1'-CH), 6.05 (br.s, 2H, 5-NH$_2$), 6.6–6.9 (br.d, 2H, CONH$_2$), and 7.3 (S, 1H, 2-CH).

EXAMPLE 11

Preparation of 2',5'-Di-O-Acetyl-3'-Neopentoxycarbonyl-AICA Riboside

To an ice-cold solution of 1.85 g 3'-neopentoxy-carbonyl-AICA-riboside in 25 ml pyridine, 0.25 ml acetic anhydride was added slowly. The resulting mixture was stirred at room temperature for about three hours. TLC (on silica gel, using methylene chloride:methanol 9:1) of the reaction mixture indicated that the reaction was complete. A 0.5 ml aliquot of methanol was added to the reaction mixture which was then evaporated under high vacuum to give a syrupy residue. The residue was coevaporated with DMF (2×10 ml). The resulting product was dissolved in 100 ml methylene chloride and extracted twice with 25 ml of 5% aqueous sodium bicarbonate solution. The organic layer was dried over anhydrous sodium sulfate and then evaporated. The residue was crystallized from hot ethyl acetate to give 1.7 g. of the above-identified compound, melting point 160°–161°C.

IR(KBr)cm$^1$: 3000–4000 (broad peaks, NH$_2$, CONH$_2$), 1740–1775 (—OCOCH$_3$ and O-COO-neopentyl).

$^1$H-NMR (DMSO-d$_6$), δppm: 0.9 (5, 9H, t-butyl), 2.05 (2s, 6H, 2'-COCH$_3$ and 3'-COCH$_3$), 3.8–3.95 (q, 2H, 5'-CH$_2$), 4.2–4.4 (m, 3H, 4'-CH and —CH$_2$— of neopentyl side chain), 5.25 (m, 1H, 3'-CH), 5.65 (t, 1H, 2'-CH), 5.9 (d, 1H, 1'-CH), 6.0 (br.s, 2H, 5-NH$_2$), 6.7–6.9 (br.d, 2H, 4-CONH$_2$) and 7.4 (s, 1H, 2-CH).

EXAMPLE 12

Preparation of 5'-O-Acetyl-3'-Isobutoxycarbonyl-AICA-Riboside and 5'-O-Acetyl-2'-Isobutoxycarbonyl-AICA Riboside To an ice-cold solution of 4.0 g 5'-O-Acetyl-AICA Riboside (the product of Example 4) in 10 ml pyridine and 10 ml DMF, a solution of 2.6 g isobutylchloroformate in 10 ml methylene chloride was added over a period of about 30 minutes. The reaction mixture was allowed to warm to room temperature over about three hours at the end of which TLC (silica gel with methylene chloride:methanol 9:1) indicated that the reaction was complete. A 1 ml aliquot of methanol was added to the reaction mixture and the solvents were removed under high vacuum. The residue was coevaporated with DMF (2×10 ml) and chromatographed on a silica gel column, eluting with methylene chloride:methanol (9:1). The fractions having identical TLC patterns were pooled and evaporated (under high vacuum) to give a colorless glassy product. The glassy product was dried under high vacuum to give 2.3 g product. The $^1$H-NMR of this product indicated that it was a mixture of 5'-O-acetyl-3'-isobutoxycarbonyl-AICA riboside and 5'-O-acetyl-2'-isobutoxycarbonyl-AICA riboside in a ratio of about 2:1 based on a comparison of the areas under the peaks for the aromatic proton.

IR (KBr) cm$^{-1}$: 3020, 3240–3500 (OH, NH$_2$, CONH$_2$ etc.)

$^1$H-NMR (DMSO-d$_6$), δppm: 0.8–1.0 (2d, 6H, 2CH$_3$ groups of isobutyl side chain), 1.8–2.0 (m, 1H, CH of the isobutyl side chain), 2.05 (2s, 3H, COCH$_3$), 3.85–3.95 (2d, 2H, CH$_2$—O— of the isobutyl side chain), 7.3 (s, 1H, 2-CH of the 5'-O-acetyl-3'-isobutoxycarbonyl-AICA riboside molecule) and 7.4 (s, 1H, 2-CH of the 5'-O-acetyl-2'-isobutoxycarbonyl-AICA riboside molecule). The ratio of those last listed peaks represented the relative percent of 5'-O-acetyl-3'-isobutoxycarbonyl-AICA riboside and 5'-O-acetyl-2'-isobutoxycarbonyl-AICA riboside in the composition as a whole as about 66% and 33%, respectively.

EXAMPLE 13

Preparation of 5-N,N-Dimethylaminomethylene-AICA Riboside

A mixture of 10.0 g 2',3',5'-tri-O-acetyl-AICA riboside, 50 ml DMF and 15 ml N,N-dimethylformamide dimethyl acetyl was stirred at room temperature for about 18 hours. The solvent and unreacted reagent were removed by evaporation under reduced pressure. The residue was dried under high vacuum for 12 hours at 40° C. to give a syrupy residue. The residue was dissolved in 30 ml dry cyclohexylamine. The resulting mixture was stirred overnight. The solvent was removed by evaporation under reduced pressure to give a gum. The gum was crystallized from ethanol to give 4.2 g of the above-identified compound as white crystals, melting point 173°–175° C.

$^1$H-NMR (MeOH-d$_4$), δppm: 3.0–3.05 (2s, 6H, N(CH$_3$)$_2$), 3.75 (m, 2H, 5'-CH$_2$), 4.0 (q, 1H, 4'-CH), 4.2 (t, 1H, 3'-CH), 4.35 (t, 1H, 2'-CH), 5.8 (d, 1H, 1'-CH), 7.7 (s, 1H, 2-CH), and 8.25 (s, 1H, 5-N=CH—N ).

EXAMPLE 14

Preparation of AICA Riboside-5'-N-Butylcarbamate

To a solution of 2.6 g AICA riboside dissolved in 20 ml DMF, 5.0 g n-butylisocyanate was added in portions over 72 hours. The reaction mixture was evaporated to dryness under vacuum. The residue was applied to a 350 ml silica gel column, prepared with methylene chloride: methanol (10:1) and eluted with methylene chloride methanol (9:1). One hundred milliliter fractions were collected. Fractions 26 to 30 (which contained the desired product) were pooled and evaporated to dryness to give 0.6 g of the above-identified product (yield about 16%).

$^1$H-NMR (DMSO-d$_6$), δppm: 0.9 (t, 3H, CH$_3$—), 1.1–1.5 (m, H, —CH$_2$—CH$_2$—), 3.0 (q, 2H, CH$_2$—NH), 4.0 (br.s, 2H, 5'-CH$_2$), 4.1–4.4 (m, 3H, 2'-CH, 3'-CH and 4'-CH), 5.3–5.5 (m, 2H, 2'-OH and 3'-OH), 5.8 (br.s, 1H, 1'-CH), 6.0 (br.s, 2H, NH$_2$), 6.8 (br.d, 2H, CONH$_2$), 7.3 (s, 1H, 2-CH).

EXAMPLE 15

Preparation of AICA Riboside-5'-T-Butylcarbamate

The above-identified compound was prepared according to the procedure described in Example 14 substituting t-butylisocyanate for n-butylisocyanate in the reaction mixture. The above-identified compound was isolated by chromatography using a silica gel column to give a yield of approximately 8%.

$^1$H-NMR (DMSO-d$_6$), δppm: 1.1 (S, 9H (CH$_3$)$_3$—C—), 4.0 (m, 3H, 4'-CH and 5'-CH$_2$), 4.1 (m, 1H, 2'-CH), 4.3 (m, 1H, 3'-CH), 5.2–5.5 (br.m, 3H, 2'-OH, 3'-OH, and 1'-CH), 5.8 (br.s, 2H, NH$_2$), 5.9 (br.s, 1H, CONH$_2$), 6.3 (br.d, 2H, CONH$_2$), 7.3 (S, 1H, 2-CH).

EXAMPLE 16

Preparation of 5-AMINO -2,3'5'-Tri-O-Acetyl-1-β-D-Ribofuranosylimidazole-4-Carboxamide ("AICA Riboside-Triacetate)

To a well-stirred, ice-cooled suspension of 50.0 g AICA riboside in 500 ml pyridine, 72 ml acetic anhydride was added over a period of 15 minutes. The cooling bath was removed; stirring of the mixture was continued for four hours during which a clear solution formed. TLC of a small aliquot drawn and evaporated indicated that the reaction was complete. The reaction vessel was cooled in ice and treated with 5 ml methanol. Pyridine was removed by evaporation under high vacuum. The residue was co-evaporated with N,N-dimethyl-formamide (3×150 ml). The tan-colored viscous product obtained was dissolved in ethanol. The resulting mixture was seeded with a few crystals of 2',3',5'-triacetyl AICA riboside. The crystalline product formed after 24 hours and was collected by filtration, washed with ice cold ethanol and dried under vacuum (40° C.) to give 65.0 g of the above-identified product, melting point 128°–130° C.

The filtrate and washings were combined and evaporated down to about 50 ml and seeded with 2',3',5'-triacetyl AICA riboside crystals to obtain an additional 7.0 g of product. Thus, giving a total yield of 72.0 g.

EXAMPLE 17

Preparation of 5-Amino-5'-Isobutyryl-1-β-D-Ribofuranosylimidazole-4-Carboxamide ("5'-Isobutyryl-AICA-Riboside")

To an ice-cooled solution of 14.9 g 2',3'-isopropylidene-AICA riboside and 6.1 g 4-N,N-dimethylamino-pyridine in 150 ml N,N-dimethylformamide, 8.69 g isobutyric anhydride (10% excess) was added over a period of 15 minutes. The cooling bath was removed and the reaction mixture stirred at room temperature overnight. TLC of a small aliquot of the reaction mixture which was drawn and worked up indicated that the reaction was complete. The reaction mixture was treated with 5 ml methanol and evaporated under reduced pressure. The syrupy product so obtained was treated with 100 ml of 60% formic acid and allowed to stand at room temperature for 48 hours. Water and formic acid were removed by evaporation under reduced pressure. The residue was chromatographed using a silica gel column with methylene chloride:methanol (9:1) as the solvent phase. The solvent was evaporated to give a syrupy product which was then stirred in hot toluene. The toluene was decanted. The residue was ground with hexane. The solid product formed and was collected by filtration, washed with hexane and dried under vacuum to give 10.2 g of the above-identified product.

IR(KBr)cm$^1$, 3500–2800 (OH,NH$_2$), 1710

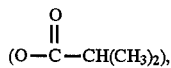

1650 (CONH$_2$). NMR (DMSO-d$_6$), δppm. 0.9–1.1 (2d,6H, 2CH$_3$), 2.5–2.65 (m, 1H, C—CH), 4.0 (m, 2H, 5'-CH$_2$), 4.15–4.3 (m, 3H, 2'-CH, 3'-CH, and 4'-CH) 5.35(d,1H, 1'-CH),5.4–5.6(2d, 2H, 2'-OH and 3'OH) 5 8 (br.s, 2H, NH$_2$), 6.6–6.95(br.d, 2H, CONH$_2$), and 7.3 (S, 7H, 2-CH).

EXAMPLE 18

Preparation of 5-AMINO-5'-Pivaloyl-1-β-D-Ribofuranosylimidazole-4-Carboxamide ("5'-Pivaloyl-AICA Riboside")

To an ice-cooled solution of 14.9 g 2',3'-isopropylidene-AICA riboside in N,N-dimethylformamide, 10.23 g pivalic anhydride and 6.1 g 4'N,N-dimethyl-aminopyridine were added in sequence. The cooling bath was removed and the reaction mixture as stirred at room temperature for 24 hours. TLC of a small aliquot of the reaction mixture drawn and worked up indicated that the reaction was complete. The reaction mixture was treated with 5 ml methanol and evaporated to dryness under high vacuum. The residue so obtained was treated with 100 ml of 60% formic acid and then allowed to stand at room temperature for 48 hours. Formic acid and water were removed by evaporation under reduced pressure. The resulting residue was chromatographed on a silica gel column using methylene chloride:methanol (9:1) as the solvent phase. The syrupy product obtained after evaporation of the solvent was stirred in hot toluene. The toluene was decanted and the product was ground with 150 ml hexane. The solid product formed and was collected by filtration, washed and hexane and dried under vacuum to give 11.5 g of the above-identified product.

IR(KBr) cm$^1$, 3500–2900 (OH,NH$_2$), 1720

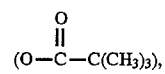

1645 (CONH$_2$).

NMR(DMSO-d$_6$), δppm, 1.15 (s, 9H, 3CH$_3$), 3.95–4.05 (m, 2H, 5'-CH$_2$), 4.15–4.3 (m, 3H, 2'-CH, 3'-CH, and 4'-CH), 5.35 and 5.55 (2d, 2H, 2'OH, and 3'-OH), 5.48 (d, 1H, 1'-CH), 5.75–5.9 (br.s, 2H, 5-NH$_2$), 6.6–6.9 (br.d, 2H, CONH$_2$) 7.25 (s,1H, 2-CH).

EXAMPLE 19

Preparation of 5-AMINO-5'-n-Butyryl-1-β-Ribofuranosylimidazole-4-Carboxamide ("5'-n-Butyryl-AICA Riboside")

To an ice-cooled solution of 12.2 g 2', 3'-isopropylidene AICA riboside in a mixture of 50 ml N,N-dimethylformamide and 50 ml pyridine, 5.0 ml n-butyric anhydride was added over a period of 10 minutes. The cooling bath was removed and the reaction mixture was stirred for 20 hours. TLC of a small aliquot of the reaction mixture drawn and evaporated indicated that the reaction was complete. The reaction mixture was treated with 5 ml methanol and evaporated under high vacuum. The residue was coevaporated twice with 50 ml N,N-dimethylformamide. The resulting product was dissolved in 120 ml of 60% formic acid and then allowed to stand at room temperature for 48 hours. Water and formic acid were removed by evaporation under high vacuum. The residue was chromatographed on a silica gel column using methylene chloride:methanol (9:1) as the solvent phase. The sticky product obtained after evaporation of solvent was triturated with hot toluene. The toluene was decanted. The product was ground with hexane. The amorphous powder which formed was collected by filtration, washed with hexane, and dried under high vacuum to give 2.7 g of the above-identified product.

IR(KBr)cm$^{-1}$, 3500–2900 (OH, NH$_2$, etc ), 1695

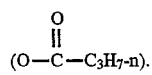
(O—C—C$_3$H$_7$-n).

NMR(DM50-d$_6$), δppm. 0.8–0.95(t, 3H, CH$_3$), 1.5(m, 2H, —CH$_2$ attached to CH$_3$), 2.18–2.2(t, 2H,

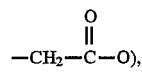
—CH$_2$—C—O), 3.95–4.1(m, 2H, 5'-CH$_2$), 4.15–4.35(m, 3H, 2'-CH, 3'-CH, and 4'-CH), 5.35(d, 1H, 1'-CH), 5.4–5.6 (2d, 2H, 2'-OH and 3'-OH) 5.75–5.9(br.s, 2H, 5-NH$_2$), 6.6–6.9(br.d, 2H, CONH$_2$), 7.3(s, 1H, 2-CH).

By using the procedures described in Examples 1 to 19 and in the Detailed Description of the Invention, and using the appropriate starting materials and reagents the compounds listed in Table I were prepared. Also, by using the procedures described in Examples 1 to 19 and in the Detailed Description of the Invention, the compounds listed in Tables II and III are prepared.

EXAMPLE A

Activity in Inhibiting HTL-Induced Seizures

Compounds were tested for their activities in inhibiting HTL-induced seizures in rats.

Animals used were male Swiss Webster mice weighing 21–30 grams (Charles River Breeding Labs, Wilmington, Mass.). All animals were adapted to the laboratory for at least 5 days prior to use.

All solutions to be injected were prepared as a single injection cocktail at a concentration such that 1 ml per 100 g of body weight yielded the desired dose. The solutions were compounded as follows: Homocysteine Thiolactone—HCl (HTL-HCl) (Sigma Chemical Company, St. Louis, Mo.) was dissolved in distilled water and the pH adjusted to 6.7 with NaOH. Pentylenetetrazol (PTZ) was dissolved in 0.9% saline. Prodrug compounds or AICA riboside (Sigma) when used alone was dissolved in distilled water. All solutions containing Mioflazine (Janssen Pharmaceuticals) were prepared at a final DMSO concentration of 10–15% as were the Dipyridamole (Sigma) solutions. N-ethyl-carboxamide adenosine, NECA (Sigma) and Flunitrazepam (Hoffman La Roche) injections were prepared in a final ethanol concentration of 0.2%. In all cases carrier control solutions of carrier were injected that were matched for both tonicity and solvents to the test solutions. All test and control solutions were injected via a bolus, I.P., using a 27 gauge needle. HTL and PTZ were injected subcutaneously in the upper back of the animal.

Animals were preinjected with either control solution containing only carrier or test solution containing candidate compound (prodrug or AICA riboside) and carrier in groups of 6–8 per test solution or control. The seizure inducing composition solution was injected at a specific time interval thereafter (ranging from 15 minutes to several hours, most experiments utilized a 30 minute interval). After injection of the seizure inducing composition animals were isolated in separate cages and observed for the onset of a seizure. In most experiments animals were scored as being fully protected from a seizure if they failed to seize for a period 2–3 hours following homocysteine thiolactone (HTL) injections (carrier control latency about 20 minutes) and 1 hour after PTZ administration (carrier control seizure latency of 4 minutes). Seizures noted were either clonic or clonic-tonic in nature and varied in severity from forelimb clonus to full tonic extension of hind limbs and forelimbs. In all experiments the seizure latency was also noted as was the mortality rate in animals having seizures. The overt character of both the PTZ and HTL seizures were quite similar, although the latency of the former was markedly shorter.

Results of testing one of the compounds of the present invention, 3'-isobutoxycarbonyl AICA riboside (Prodrug A, Compound 1 of Table I), and AICA riboside for prevention of HTL induced seizures are shown in FIG. 1.

EXAMPLE B

Adenosine, AICA Riboside and ZMP Levels in Ischemic Heart Tissue

Prodrug compounds of the present invention and AICA riboside were tested for their activity in enhancing the production of adenosine and increasing production of AICA riboside from ZMP in ischemic heart tissue in rats.

Samples of heart tissue after ischemia were analyzed for nucleoside and nucleotide levels. Samples were measured for adenosine, AICA riboside and ZMP concentrations by HPLC.

Figure 3:
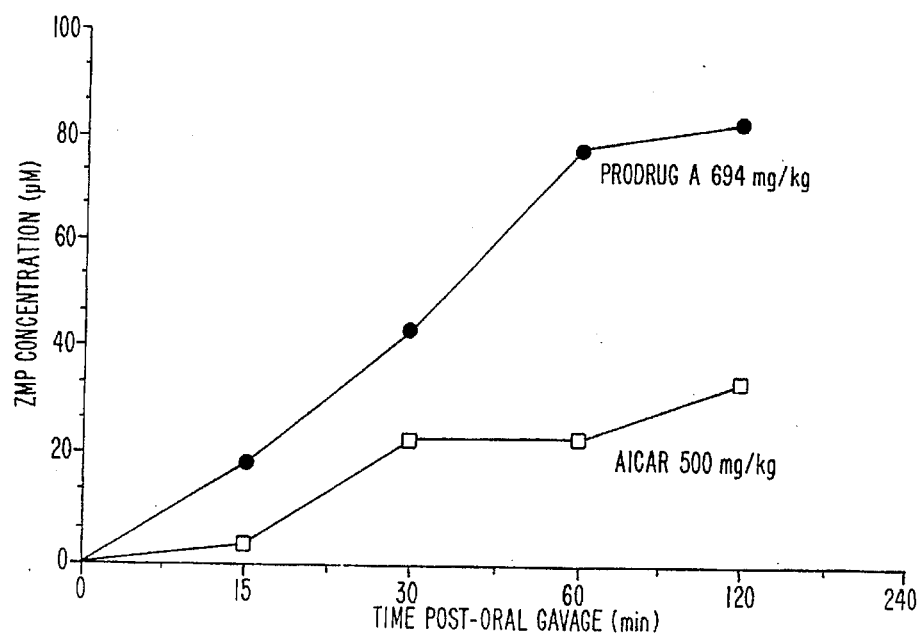
FIG. 3 depicts the effects of oral administration of AICA riboside and Prodrug A on ZMP concentration in rat heart tissue.

A comparison of adenosine production induced by saline, AICA riboside and Prodrug A (Compound 1 of Table I) is shown in FIG. 2. The fall in ZMP and quantitatively equivalent rise in AICA riboside level is shown in FIG. 3. The enhancement of adenosine production by Prodrug A as compared with an equimolar dose of AICA riboside without a corresponding high AICA-riboside level is tabulated in Table IV.

EXAMPLE C

Activity in Protection Against Ischemic Injury in Skin Flap

Compounds were tested for their activity in protecting against ischemic injury in a skin flap model in rats.

Animals were pretreated with AICA riboside or AICA riboside plus adenosine deaminase (ADA) 45 minutes before surgery or, as a positive control, superoxide dismutase (SOD) was used at the time of surgery. A skin flap was raised on the abdomen of a rat for 6 hours and then sewn down. The percent viability of the flaps was evaluated at 3 days post-surgery.

Results are tabulated in Table V.

Animals treated with AICA riboside showed an increase in skin flap viability (compared with controls) which was statistically significant according to the Fisher Exact Test ($p<0.05$). This effect was not as pronounced in the presence of ADA, supporting the importance of adenosine's protective role in this setting.

EXAMPLE D

Enhancement of Adenosine Release by Lymphoblasts

Prodrug compounds of the present invention and AICA riboside were tested for their activity in increasing adenosine release in cell culture.

With regard to the enhanced in vitro release of adenosine, a human splenic lymphoblast cell line (WI-L2) was used to demonstrate the effect of AICA riboside and prodrugs of the present inventions of the cell line have been described and properties of the cell line have been described by Hershfield et al. in Science, Vol. 197, p. 1284, 1977. The cell line was maintained in RPMI 1640 cell culture media supplemented with 10% fetal calf serum and 2 mM glutamine and equimolar concentrations of prodrug or AICA riboside and grown for 36 hours in an atmosphere of 5% carbon dioxide in air. Fetal bovine serum contains purines and purine metabolizing enzymes; however, and to establish the effect of AICA riboside or prodrug during 2-deoxyglucose exposure, the WI-L2 cells were incubated in RPMI 1640 glucose-deficient medium supplemented with 10% heat-inactivated, dialyzed fetal bovine serum, 2 mM glutamine, and 1 µM deoxycoformycin.

Catabolism of cellular ATP stores was stimulated by adding 2-deoxyglucose to a final concentration of 10 mM. At sixty minutes, the amount of adenosine released by the cells into the supernatant was determined by mixing 30 microliters of chilled 4.4N perchloric acid with 300 microliters of supernatant and centrifuging the mixtures at 500×G for 10 minutes at 4° C. Each resulting supernatant was neutralized with 660 microliters of a solution containing 2.4 grams of tri-n-octylamine (Alamine 336) (General Mills) in 12.5 milliliters of 1,1,2-trichloro-1,2,2-trifluoroethane (Freon-113) solvent as described by Khym in *Clinical Chemistry*, Vol. 21, p. 1245, 1975. Following centrifugation at 1500×G for 3 minutes at 4° C., the aqueous phase is removed and frozen at −20° C. until assayed for adenosine and inosine. Adenosine was evaluated isocratically on a C-18 micro-Bondapak reverse phase column equilibrated with 4 millimolar potassium phosphate, pH 3.4:acetonitrile 60% in water (95:5 v/v) buffer. Adenosine elutes at 8–10 minutes and its identity was confirmed by its sensitivity to adenosine deaminase and by spiking with adenosine standards. Continuous monitoring was performed by absorbance at 254 and 280 nm. Peaks were quantitated by comparison with high pressure liquid chromatography analysis of suitable standards.

Figure 4:
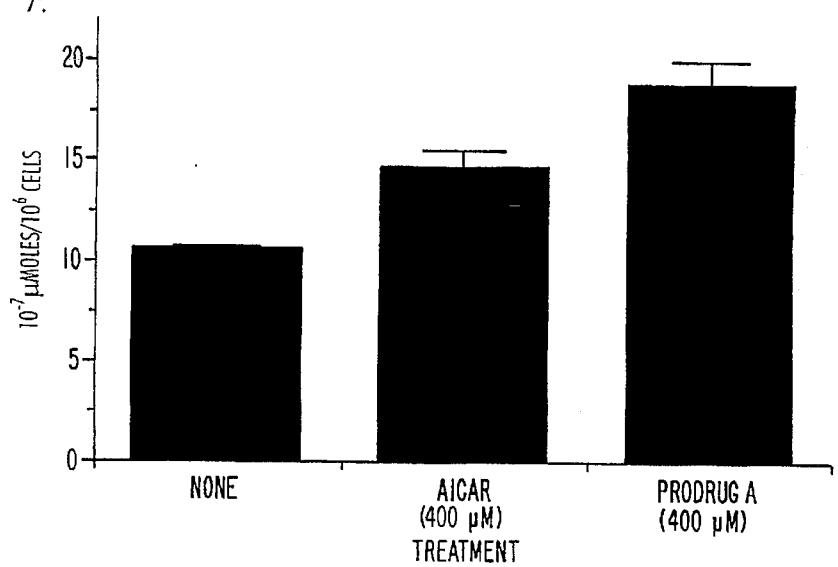
FIG. 4 depicts the effect of Prodrug A and AICA riboside on adenosine release in cell culture.

FIG. 4 shows the effect of 36 hour pretreatment with AICA riboside or Prodrug A on enhancement of adenosine release from lymphoblasts.

EXAMPLE E

Enhanced Oral Bioavailability

AICA riboside was administered to Sprague-Dawley rats at a dose of 250 mg/kg or 500 mg/kg, prodrug compounds of the present invention were administered at an equal molar dose.

At 15, 30, 60 and 120 minutes after gavage, the animals were sacrificed. The tissues were obtained and frozen immediately for nucleoside and nucleotide analysis. The tissue samples obtained were liver, heart, brain and whole blood. After initial freezing in liquid nitrogen, the tissue samples were extracted with trichloroacetic acid and neutralized with alamine freon. The tissue samples were evaluated by HPLC on a Whatman Partsil-10 (SAX) column for nucleosides and bases as described in Example 6.

In two separate experiments, at a dose equimolar to the dose of AICA riboside used, 3'-isobutoxycarbonyl AICA riboside ("Prodrug A") exhibited increased oral bioavailability as evidenced by an increase in ZMP levels in liver, whole blood and heart. Tests were run with 8 rats.

Figure 5A:
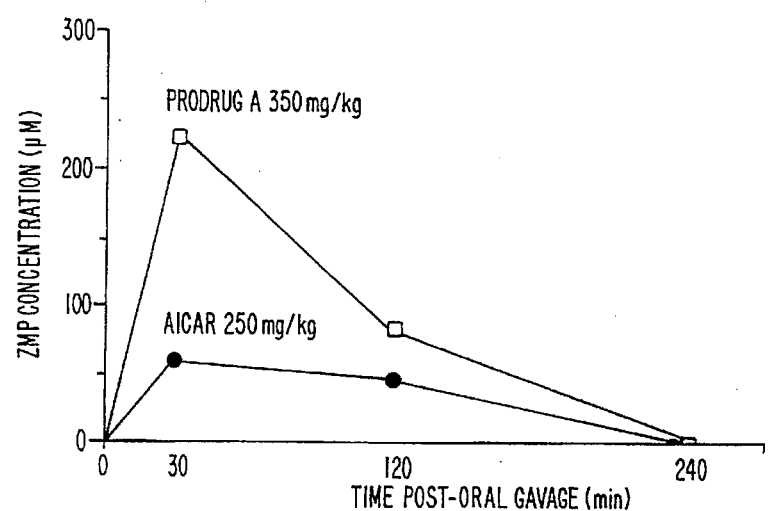
FIGS. 5A and 5B depict the effects of oral administration of AICA riboside and Prodrug A on ZMP concentration in rat liver.
Figure 5B:
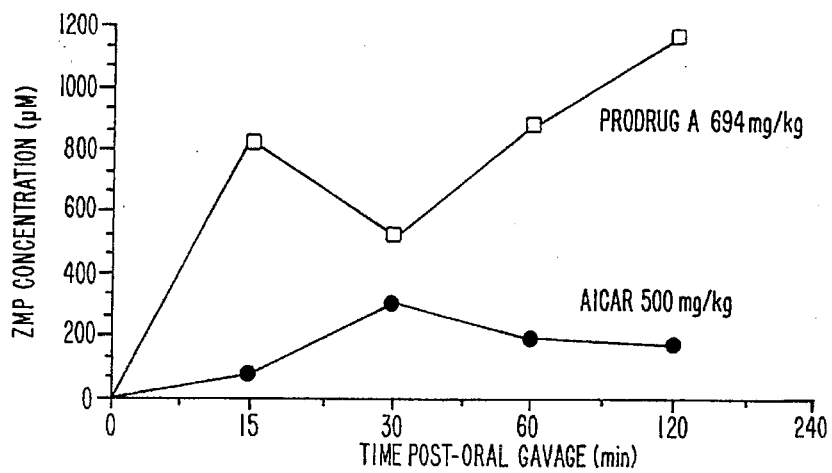

FIGS. 5(a) and (b) show ZMP concentrations in rat liver at doses of a molar equivalent of 250 mg/kg and 500 mg/kg AICA riboside.

EXAMPLE F

Effect of Length of Side Chain of 3'-Carbonate Esters of AICA Riboside on Adenosine Levels Adenosine and AMP levels resulting from the administration of equimolar amounts of AICA riboside or some 3'-carbonate esters of AICA riboside having side chain lengths of 2 to 6 carbon atoms were studied using the ischemic rat heart model of Example B.

Figure 19A:
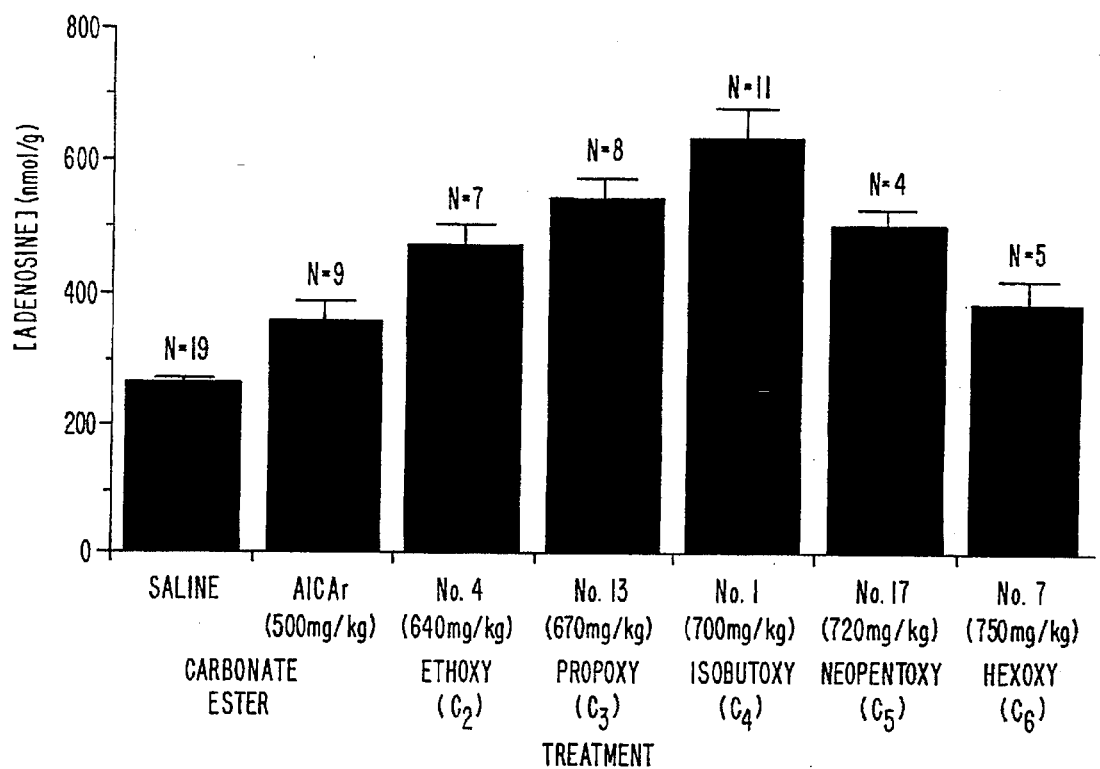
FIGS. 19A and 19B depict adenosine and AMP levels of AICA riboside and certain 3'-carbonate esters of AICA riboside in ischemic rat heart.
Figure 19B:
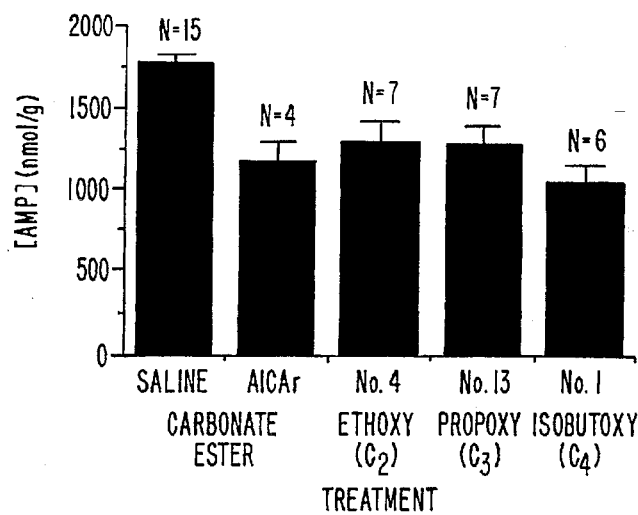

After one hour following administration of AICA riboside (500 mg/kg) or the molar equivalent of carbonate ester, the hearts were excised and incubated at 37° C. for one hour as described in Example B. Tissue adenosine and, for some of the carbonate esters, AMP levels were measured in the ischemic hearts by HPLC. Values are means ± S.E.M. Results are shown in FIGS. 19A and 19B.

EXAMPLE G

Glucose Levels in Fasted Mice

Male mice (Swiss-Webster) were injected IP with the indicated treatment. The mice were fasted for 120 minutes before treatment. Ribose and AICA riboside were formulated in saline. Glucose levels were measured on serum (heparinized blood centrifuged at 10,000×g for ten minutes). Glucose levels were measured one hour after AICA riboside administration. Results are reported in FIG. 6.

EXAMPLE H

Figure 7:
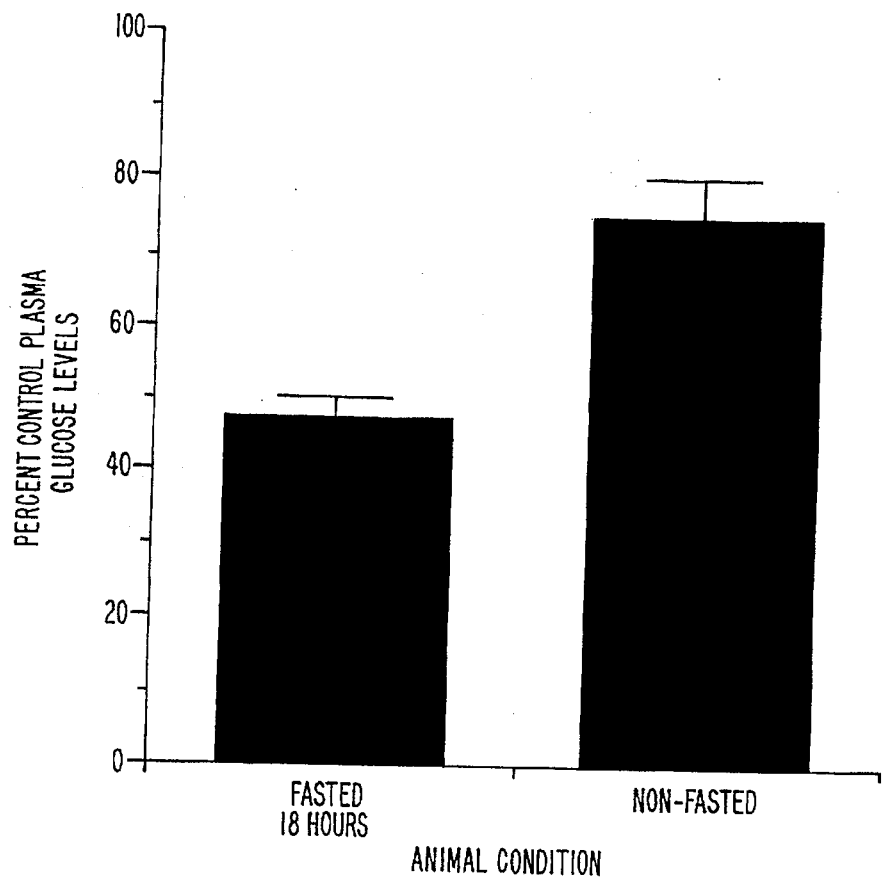
FIG. 7 depicts the effect of AICA riboside on plasma glucose in fasted and non-fasted rats.

Effect of AICA Riboside on Plasma Glucose Levels in Fasted and Non-Fasted Rats Fasted rats were fasted for 16 hours before administration of AICA riboside. Rats were given a 750 mg/kg dose of AICA riboside IP (8 animals per group). Forty minutes later blood samples were taken. Blood was centrifuged at 10,000 x/g for 10 minutes and then analyzed for glucose levels using the hexokinase procedure (See Example K). Results are shown in FIG. 7.

EXAMPLE H-2

Effect of AICA Riboside on Blood Glucose in Rabbits

Rabbits (New Zealand White) were given IV doses of AICA riboside, either 2 ml/kg (100 mg/kg) or 4 ml/kg (200 mg/kg). Blood was obtained by venipuncture before AICA riboside administration and two hours post-administration. Blood glucose concentrations before administration and two hours post-administration were measured by the hexokinase procedure (see Example K). The percent change (+/−) from pre-dose values are reported. Both dosage levels decreased blood glucose levels as compared with pre-AICA riboside administration levels. Results are tabulated in Table VI.

EXAMPLE I

Effect of AICA Riboside on Plasma Glucose Levels in Humans

Healthy male volunteers were given a 30-minute intravenous infusion of AICA riboside at doses of 25 mg/kg, 50 mg/kg or 100 mg/kg.

Figure 8:
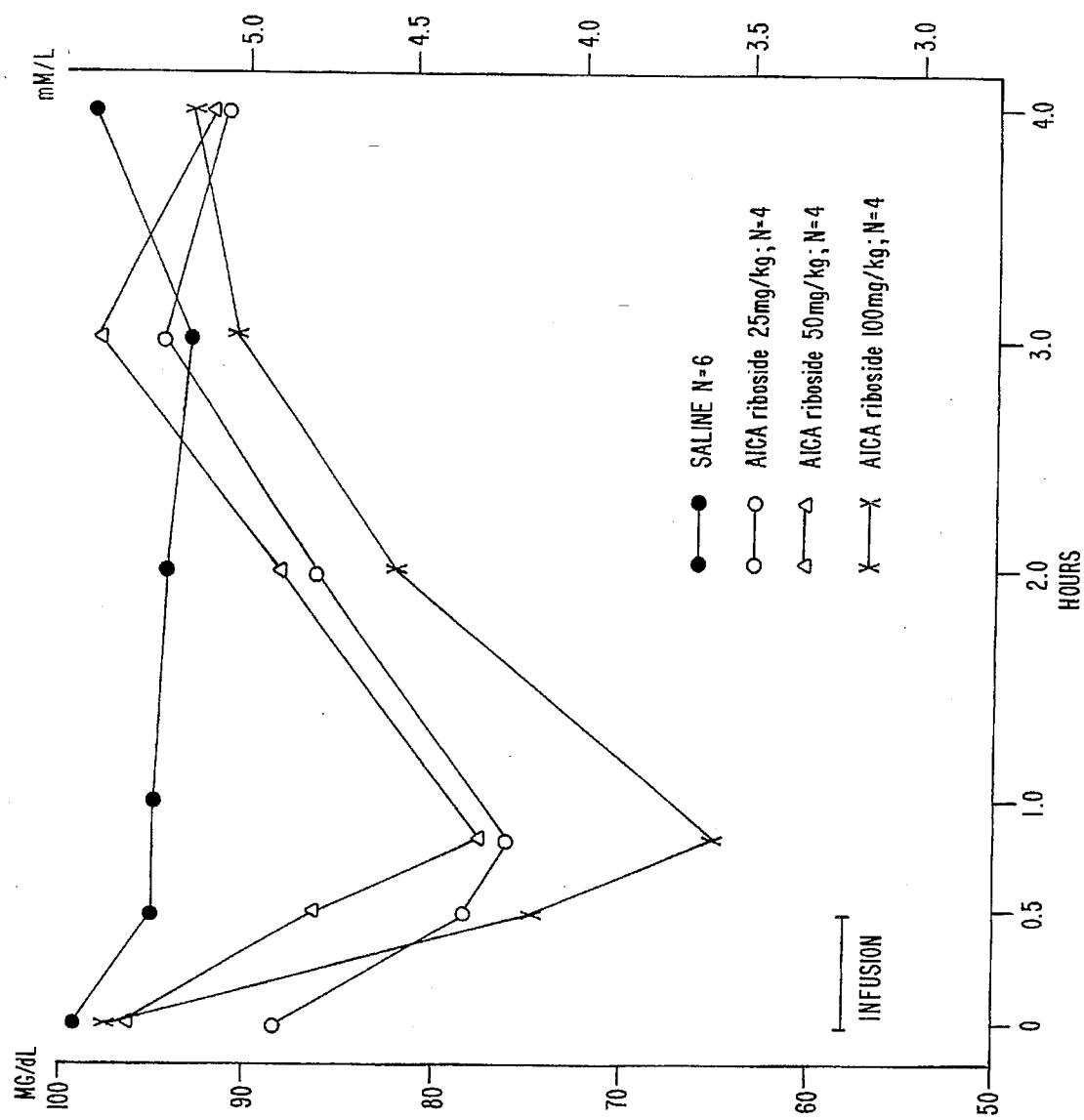
FIG. 8 depicts the effect of AICA riboside on serum glucose in humans.
Figure 9:
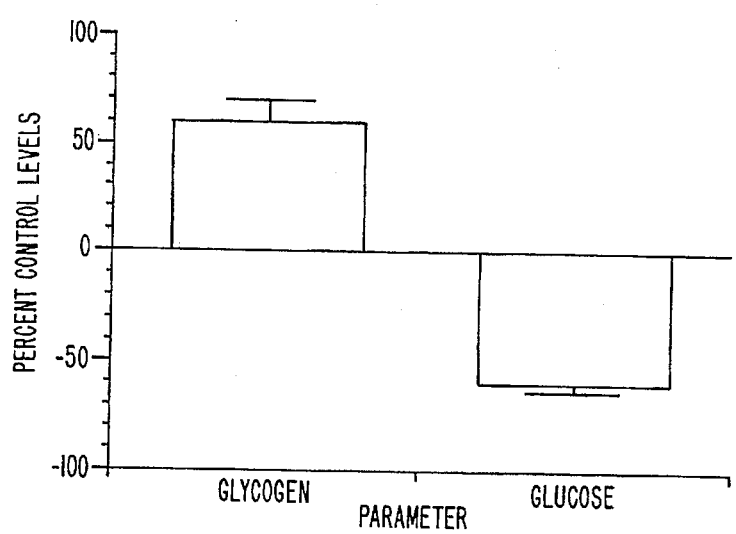
FIG. 9 depicts the effects of AICA riboside on liver glycogen.

Plasma glucose levels were monitored over a four hour period during and following the 30 minute infusion. Plasma glucose was measured by clinical chemistry autoanalyzer. The onset of the serum glucose lowering effect was evident by the end of the AICA riboside infusion period and plasma glucose reached a nadir approximately 30 minutes after the AICA riboside infusion was stopped. Recovery to euglycemic levels was complete by about three hours. Results are shown in FIG. 8.

EXAMPLE J

Effect of AICA Riboside on Liver Glycogen in Mice

Swiss Webster mice were treated with saline (as a control) or 750 mg/kg of AICA riboside administered intraperitoneally, six animals per group. The mice were sacrificed one hour post-administration. The livers were removed and extracted. Liver glycogen was determined by the method of Dubois, et al., Anal. Chem. 28:350–356 (1956). Glucose was measured by the hexokinase method (See Example K). Results are reported in FIG. 9.

EXAMPLE K

Effects of AICA Riboside on Blood Lactate and Pyruvate in Rats

AICA riboside (100, 250 or 500 mg/kg) or saline (as a control) was administered intraperitoneally to rats. Sixty minutes after AICA riboside administration, the rats were sacrificed by cervical dislocation. Blood glucose was determined spectrophotometrically measuring O.D. at 340 nm by the hexokinase method using the glucose SR Reagent (Medical Analysis Systems, Inc.) Blood lactate and pyruvate were determined spectrophotometrically measuring O.D. at 340 nm using lactate dehydrogenase in the presence of excess NAD or NADH, respectively. Values were expressed as mean +S.E.M. Results are reported in FIGS. 10A to 10D.

EXAMPLE L

Effect of AICA Riboside on Blood Glucose Levels in Conjunction with Liver ZMP Levels The association of AICA riboside-induced reduction in blood glucose with hepatic ZMP in the mouse was investigated.

AICA riboside (either 100 or 500 mg/kg) was administered intravenously by tail vein injection to mice which had been fasted for four hours. At a time of 2, 5, 10, 30 or 120 minutes post-administration, the mice were sacrificed by cervical dislocation. Blood glucose was measured spectrophotometrically, measuring O.D. at 340 nm, by the hexokinase method using the glucose SR Reagent (Medical Analysis Systems, Inc.). Portions of liver (0.2 to 0.3 g) were freeze clamped in situ, homogenized and, following centrifugation, the neutralized supernatant was analyzed by ion-exchange HPLC. Values were expressed as means +S.E.M. Results are reported in Table 11.

EXAMPLE M

Inhibition of Fructose-1,6-Diphosphatase

Inhibition of fructose-1,6-diphosphatase from rabbit liver (Sigma) by AICA riboside monophosphate (ZMP) and AMP was measured according to the assay technique described in *Methods in Enzymology* 90:352–357 (1982). Results are reported in FIG. 12.

EXAMPLE N

Plasma Insulin Levels in Humans after AICA Riboside Administration

Human (male) volunteers were given a 15-minute intravenous infusion of 50 mg/kg AICA riboside. Plasma concentrations of immunoreactive insulin was determined by RIA during and following the administration for about 4 hours. (RIA kit, hersham Clinical). Results are reported in FIG. 13.

EXAMPLE O

Hypoglycemic Effects of AICA Riboside Prodrugs

Male mice (Swiss Webster) were given equimolar amounts of either saline, AICA riboside, or compounds C1 or 10 of Table I orally. Blood glucose levels were measured one hour after administration by the glucose strip method (Chemstrip B.G.). Results are reported in FIG. 14.

EXAMPLE P

Effects of Inhibition of Adenosine Kinase on PTZ-Induced Seizures

Swiss Webster mice were given the indicated dose (100, 200 or 400 mg/kg) of the adenosine kinase inhibitor, 5'-amino-5'-deoxyadenosine, or saline (as a control) intraperitoneally. One hour later the animals were given a 75 mg/kg dose of pentylenetetrazole (PTZ) and the seizure frequency observed. Results are reported in FIG. 15.

EXAMPLE Q

Inhibition of Fructose 1,6-Diphosphatase by ZMP and Carbocyclic ZMP

The indicated concentrations (250 μm) of ZMP and carbocyclic ZMP were incorporated into the fructose 1,6-diphosphatase assay (see Example M), and the resulting activity was determined. Activity was expressed as a velocity (rate of conversion of substrate). Results are reported in FIG. 16.

EXAMPLE R

Effect of Chronic AICA Riboside Treatment on Triglyceride Levels in Diabetic Rats Rats were made diabetic by treatment with streptozocin (50 mg/kg IV) and then treated with either saline or AICA riboside (500 mg/kg, twice a day) for 22 days. Plasma triglyceride levels were analyzed 18 hours after the last injection of AICA riboside using the Sigma Procedure #334 Assay Kit (coupled assay employing lipase, glycerokinase, pyruvate kinase and lactate dehydrogenase) which measures decreases in $OD_{340}$ over time (NADH disappearance).

EXAMPLE S

Figure 18:
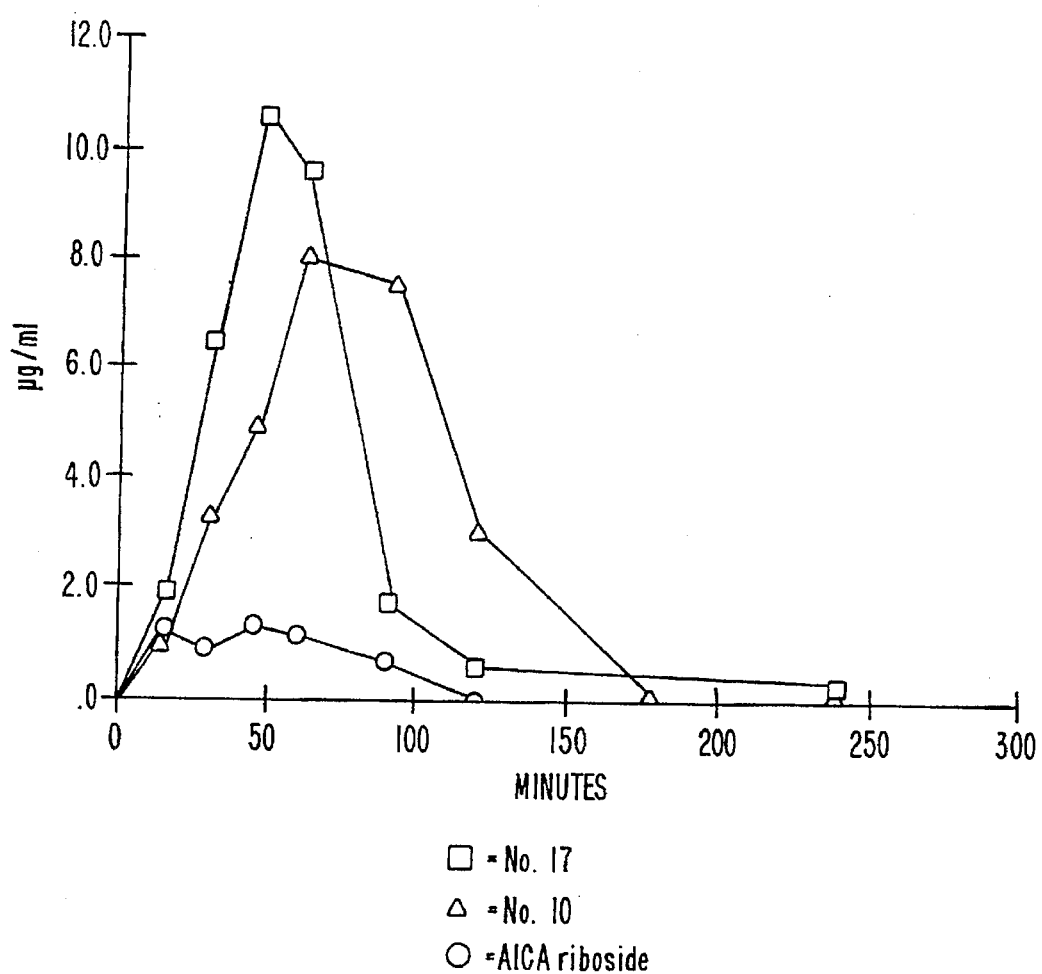
FIG. 18 depicts plasma concentrations of AICA riboside in dogs after oral administration.
Figure 20:
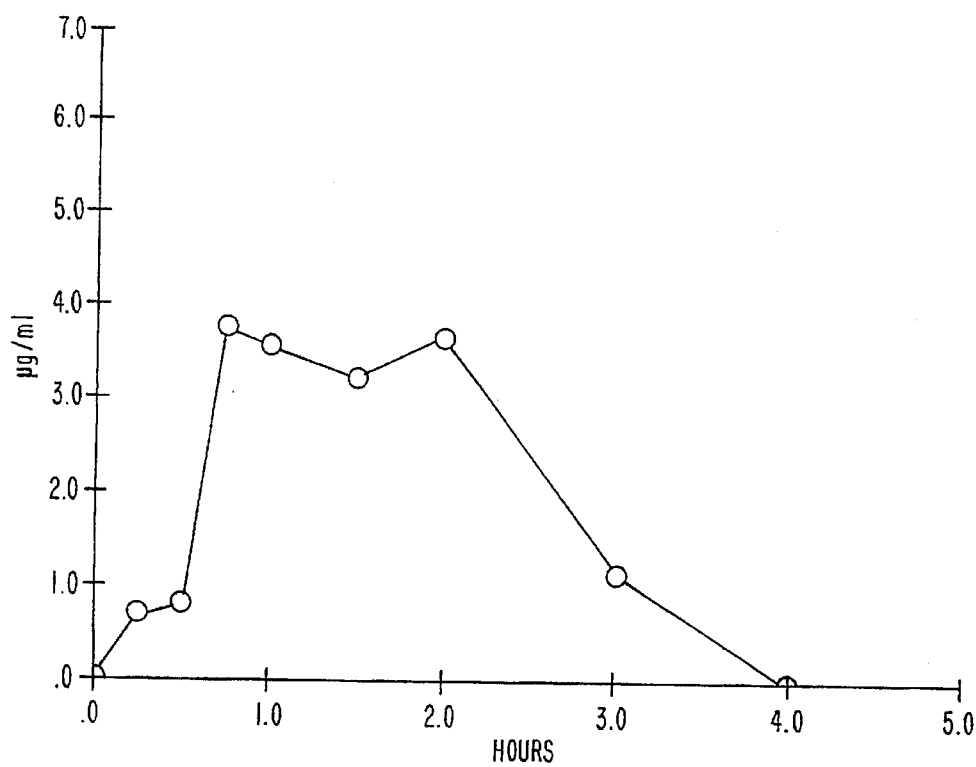
FIG. 20 depicts plasma concentration of AICA riboside in dog-following oral administration of a prodrug of AICA riboside (3,5-diacetyl AICA riboside).

Effect of Oral Administration of AICA Riboside or an AICA Riboside Prodrug on Plasma AICA Riboside Levels Plasma concentrations of AICA riboside in dogs were determined by HPLC following oral administration of 50 mg/kg AICA riboside and the (molar) equivalent amount of 50 mg/kg AICA riboside or one of two prodrugs, compounds 10 and 17 of Table I. The compounds were administered in solution in PEG 400:water (1:1). Results are shown in FIG. 18. A different prodrug, Compound 22 of Table I, was administered in solid form in a capsule (50 mg/kg). Results are shown in FIG. 20. Plasma concentration of AICA riboside was determined according to: Dixon, R., et al., "AICA riboside: Direct quantitation in ultrafiltrate of plasma by HPLC," Res. Commun. Chem. Path. Pharm., in press (1989).

EXAMPLE T

Effect of AICA Riboside on Serum Glucose Levels in Diabetic Mice

Figure 21:
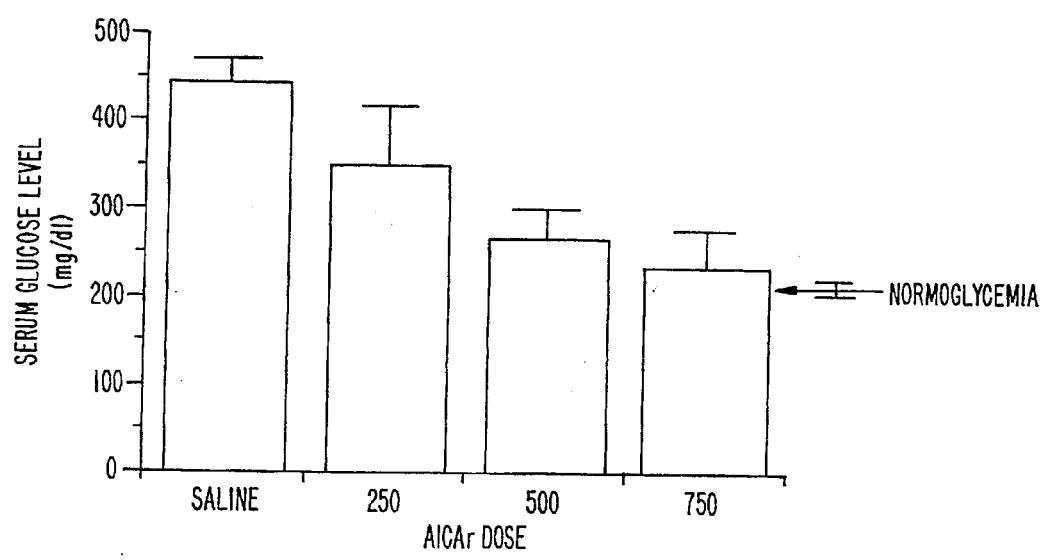
FIG. 21 depicts the effect of AICA riboside on serum glucose levels in streptozotocin-induced diabetic mice.

Mice were made diabetic by low dose Streptozotocin treatment (40 mg/kg/day for 5 days followed by a 10-day incubation period). These diabetic mice, 11 per group, were treated with the indicated dose of AICA riboside or saline in an IP bolus of 1 ml/100 g body weight. The animals were exsanguinated 1.5 hours post-administration (of AICA riboside or saline). The plasma was isolated by centrifugation and analyzed for glucose by the hexokinase/glucose-6-phosphate dehydrogenase spectrophotometric method (see Example K). Normoglycemic levels were determined from saline-treated nondiabetic mice by the same protocol. Values were expressed as mean ± sem. Results are reported in FIG. 21.

EXAMPLE U

Effect of Chronic AICA Riboside Treatment on Blood Glucose and Water Intake in Diabetic Rats Rats made diabetic with Streptozotocin (60 mg/kg, 5 days post-treatment), 9 per group, were treated twice daily with 500 mg/kg AICA riboside or with physiological saline via injection IP, except for days 6, 13 and 20 when a single 750 mg/kg dose was administered and except for days 7, 14 and 21 when no treatment was given. Blood was drawn by tail bleeds, two hours post-injection, on the days indicated, analyzed for glucose using Chemstrip bG glucose reagent strips and an Accuchek II blood glucose monitor (both from Boehringer Manheim). Data was calculated as percent of pretreated levels and expressed as mean ± sem. Results are reported in FIG. 22.

The water intake from these rats was measured by determining the amount of water lost from the individual cage water bottles each day. Values are expressed as a cumulative mean ± sem. Results are reported in FIG. 23.

EXAMPLE V

Figure 24:
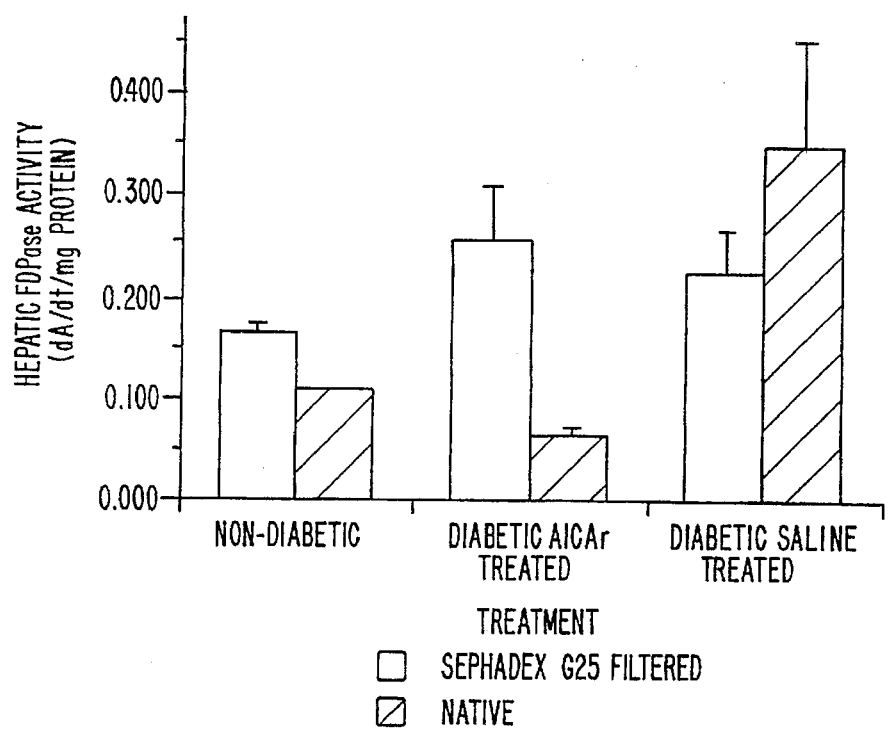
FIG. 24 depicts the effects of chronic AICA riboside treatment on hepatic fructose 1,6-diphosphatase activity in streptozotocin-induced diabetic rats.

Effects of Chronic AICA Riboside Treatment on Hepatic Fructose 1,6-Diphosphatase (FDPase) Activity in Diabetic Rats Rats made diabetic with Streptozotocin (60 mg/kg, 5 days post treatment) were treated with either 2×500 mg/kg/day AICA riboside or 0.9% saline twice a day for three weeks. Eighteen hours after the last treatment the livers were removed. Livers from the treated rats and from native rats were homogenized in 20 µM potassium phosphate buffer (pH 7.4) with 100 µM EDTA and 100 µM dithiothreitol and then centrifuged for 20 minutes at 45,000×g. FDPase activity was assayed both in this native form and following passage of the supernatant over a sephadex G25 column by the method of Marcus et al (Methods in Enzymology 90:352–356 (1982)). Protein concentrations were determined by the Bradford method (Anal. Biochem. 72:248 (1976); Anal. Biochem. 86:142 (1978)). Enzyme activity per mg protein was expressed as mean ± sem. Results are shown in FIG. 24.

EXAMPLE W

Determination of IC50 for Inhibition of FDPase by ZMP

Liver samples (from the indicated species) were homogenized in 20 mM potassium phosphate buffer (pH 7.4) with 100 µM EDTA and 100 µM dithiothreitol. The liver homogenates were centrifuged at 45,000×/g. The supernatants were passed over a sephadex G25 column and assayed for FDPase activity by the method of Marcus et al (Methods in Enzymology 90:352–356 (1982)) in the presence of ZMP over a range of concentration and in the absence of ZMP. The IC50 value was defined as the concentration of ZMP, which inhibited 50 percent of the baseline FDPase activity under the assay conditions. Results are shown in Table VII.

EXAMPLE X

Effect of AICA Riboside on Hepatic Fructose 1,6-Diphosphate Levels in Mouse

Figure 25:
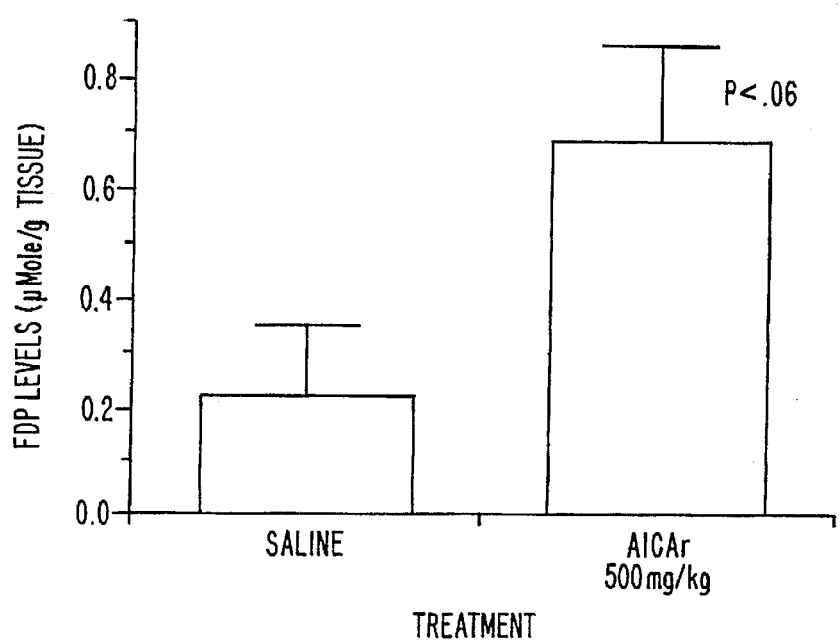
FIG. 25 depicts the effect of AICA riboside on hepatic fructose 1,6-diphosphate levels in mice.

Mice which had been fasted for 6 hours were given either an IP injection of 500 mg/kg AICA riboside or 0.9% saline. The animals were sacrificed 1.5 hours post-injection; their livers were removed and extracted into iced perchloric acid. The extracts were neutralized and analyzed for fructose 1,6-diphosphate by the method of Shrinivas et al (Biochem J. 262: 721–725 (1989)). Results are shown in FIG. 25.

EXAMPLE Y

Figure 26:
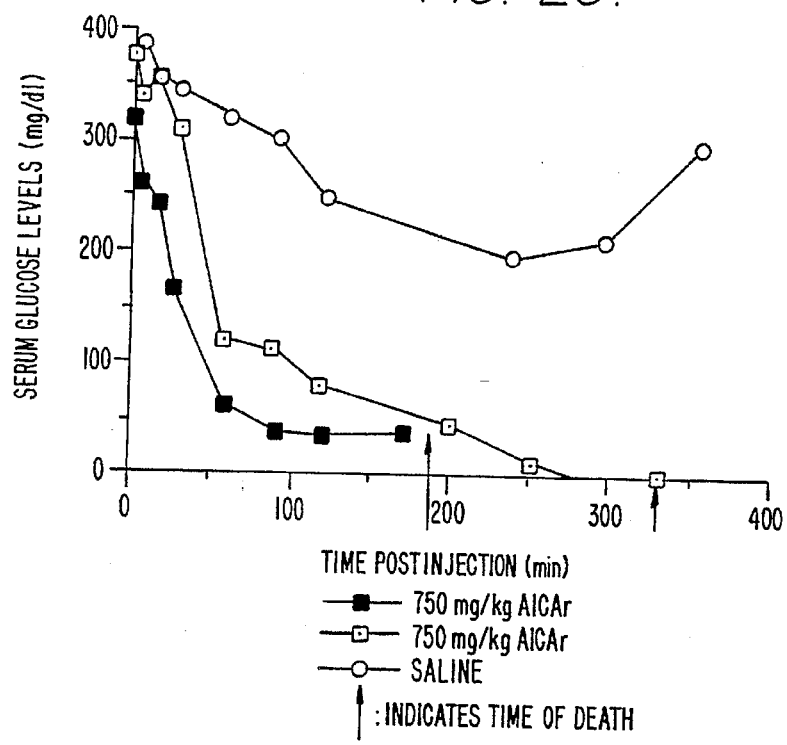
FIG. 26 depicts a comparison of the effects of the hypoglycemic agent glyburide and AICA riboside in fasted and non-fasted mice.

Comparison of Glyburide (Oral) and AICA Riboside (IP) on Blood Glucose Levels in Fasted and Non-Fasted Mice Fed or 24-hour fasted mice were treated either with vehicle, 5 mg/kg glyburide (an oral hyperglycemic agent) administered orally or 600 mg/kg AICA riboside administered IP. Either three hours post-administration or at the time of hypoglycemic seizure, whichever came first, blood was taken. The serum was isolated by centrifugation and analyzed for glucose levels by the hexokinase/glucose-6-phosphate dehydrogenase spectrophotometric assay (see Example K). Drug group values were expressed as percent of vehicle levels. Results are shown in FIG. 26.

EXAMPLE Z

Effect of AICA Riboside on Serum Glucose Levels in Diabetic Rats

Figure 27:
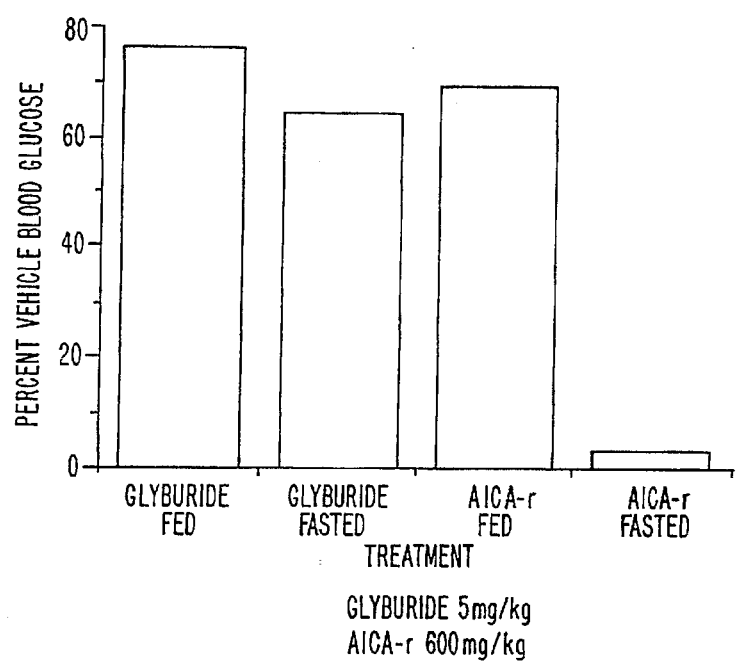
FIG. 27 depicts the effect of AICA riboside on serum glucose levels in streptozotocin-induced diabetic rats.

Sprague-Dawley rats (200 g each) made diabetic with Streptozotocin (55 mg/kg, 4 days post-treatment) were anesthetized with diethyl ether. After anesthetizing, an incision was made and a cannula of silastic medical grade tubing (0.020 inch I.D/0.037 inch O.D.) was inserted into the right jugular 5 mm rostral to the clavicle and extended 20 mm toward the heart. The cannula was anchored and exteriorized through the back of the neck, filled with heparized saline (500 U/ml) and tied off. The following day, the rats were given an IP injection of either 750 mg/kg AICA riboside or physiological saline. Serial blood draws were made via the cannula. Serum was isolated by centrifugation and was analyzed for glucose by the hexokinase/glucose-6-phosphate dehydrogenase method (see Example K). Results are reported in FIG. 27.

EXAMPLE AA

Evaluation of Oral Bioavailability of AICA Riboside Prodrugs

The bioavailability of AICA riboside after oral administration of either AICA riboside or one of the AICA riboside prodrugs of the present invention was evaluated in dogs. Plasma concentrations of AICA riboside and intact prodrug were measured using HPLC. (See Dixon, R., et al., Res. Commun. Chem. Path. Pharm. 65:405–408 (1989)). Bioavailability of AICA riboside was evaluated in terms of the time required to reach maximum plasma concentration (Tmax), the maximum concentration achieved (Cmax) and the area under the plasma concentration-time curve (AUC) from time zero to the last measurable plasma concentration. Absolute bioavailability (F %) was calculated by dividing the AUC for AICA riboside following oral administration of the prodrug (or AICA riboside itself) by the AUC following intravenous administration of an equivalent amount of AICA riboside (100% bioavailability). Results are tabulated in Table VIII.

TABLE I
Compounds of the formula:
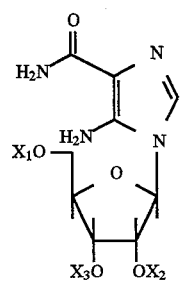
| Compound | $X_1$ | $X_2$ | $X_3$ |
|---|---|---|---|
| 1 | —H | —H | —COCH$_2$CH(CH$_3$)$_2$ |
| 2 | —COCH$_2$CH(CH$_3$)$_2$ | —COCH$_2$CH(CH$_3$)$_2$ | —H |
| 3 | —COCH$_2$CH$_3$ | —H | —H |
| 4 | —H | —H | —COCH$_2$CH$_3$ |
| 5 | —COCH$_2$CH$_2$CH$_3$ | —H | —H |
| 6 | —COCH$_2$CH$_2$CH$_3$ | —COCH$_2$CH$_2$CH$_3$ | —H |
| 7 | —H | —H | —CO—(CH$_2$)$_5$CH$_3$ |
| 8 | —H | —CCH$_3$ | —CCH$_3$ |
| 9 | —H | —CCH$_3$ | —H |
| 10 | —CCH(CH$_3$)$_2$ | —H | —H |
| 11 | —CC(CH$_3$)$_3$ | —H | —H |
| 12 | —C(CH$_{14}$)CH$_3$ | —H | —H |
| 13 | —H | —H | —COCH$_2$CH$_2$CH$_3$ |
| 14 | —H | Together | |
| | | O | |
| 15 | —H | —COCH$_2$CH(CH$_3$)$_2$ | —H |
| 16 | —COCH$_2$CH(CH$_3$)$_2$ | —H | —H |

TABLE I-continued

Compounds of the formula:

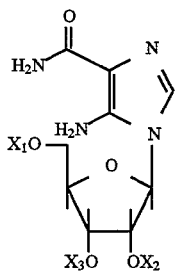

| Compound | $X_1$ | $X_2$ | $X_3$ |
|---|---|---|---|
| 17 | —H | —H | —COCH$_2$C(CH$_3$)$_3$ (C=O) |
| 18 | —H | —H | —CO-cyclopropyl (C=O) |
| 19 | —CO-cyclopropyl (C=O) | —H | —H |
| 20 | —COCH$_2$C(CH$_3$)$_3$ (C=O) | —H | —H |
| 21 | —CCH$_3$ (C=O) | Together | |
| 22 | —CCH$_3$ (C=O) | —H | —CCH$_3$ (C=O) |
| 23 | —CCH$_3$ (C=O) | —CCH$_3$ (C=O) | —COCH$_2$C(CH$_3$)$_3$ (C=O) |
| 24 | —CCH$_3$ (C=O) | —H | —COCH$_2$C(CH$_3$)$_3$ (C=O) |
| 25 | —CCH$_3$ (C=O) | —COCH$_2$C(CH$_3$)$_2$ (C=O) | —H |
| 26 | —CCH$_2$CH$_2$COOH (C=O) | —CCH$_2$CH$_2$COOH (C=O) | —CCH$_2$CH$_2$COOH (C=O) |
| 27 | —CNHCH$_2$CH$_2$CH$_2$CH$_3$ (C=O) | —H | —H |
| 28 | —CNHC(CH$_3$)$_3$ (C=O) | —H | —H |
| 29 | —CCH$_2$CH$_2$CN(CH$_2$CH$_3$)$_2$ (C=O)(C=O) | —H | —H |
| 30 | —CCH$_2$CH$_2$CH$_3$ (C=O) | —CCH$_2$CH$_2$CH$_3$ (C=O) | —CCH$_2$CH$_2$CH$_3$ (C=O) |
| 31 | —CCH$_2$CH$_2$CH$_3$ (C=O) | —H | —H |

TABLE I-continued

Compounds of the formula:

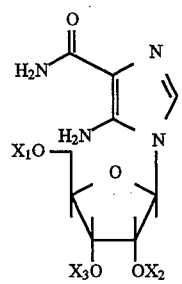

| Compound | $X_1$ | $X_2$ | $X_3$ |
|---|---|---|---|
| 32 | $-\overset{O}{\underset{\|}{C}}CH_2CH_3$ | $-\overset{O}{\underset{\|}{C}}CH_3$ | $-\overset{O}{\underset{\|}{C}}CH_3$ |
| 33 | $-\overset{O}{\underset{\|}{C}}CH_2CH_3$ | $-H$ | $-H$ |
| C1 | $-\overset{O}{\underset{\|}{C}}CH_3$ | $-\overset{O}{\underset{\|}{C}}CH_3$ | $-\overset{O}{\underset{\|}{C}}CH_3$ |
| C2 | $-\overset{O}{\underset{\|}{C}}CH_2CH_3$ | $-\overset{O}{\underset{\|}{C}}CH_2CH_3$ | $-\overset{O}{\underset{\|}{C}}CH_2CH_3$ |
| C3 | $-\overset{O}{\underset{\|}{C}}CH_3$ | $-H$ | $-H$ |
| C4 | $-\overset{O}{\underset{\|}{C}}C_6H_5$ | $-\overset{O}{\underset{\|}{C}}C_6H_5$ | $-\overset{O}{\underset{\|}{C}}C_6H_5$ |

TABLE II

Compounds of the formula:

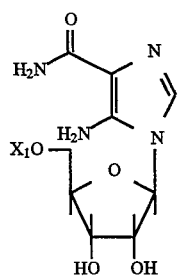

| Compound | $X_1$ |
|---|---|
| 34 | $-\overset{O}{\underset{\|}{C}}OCH(CH_3)_2$ |
| 35 | $-\overset{O}{\underset{\|}{C}}OC(CH_3)_3$ |
| 36 | $-\overset{O}{\underset{\|}{C}}O(CH_2)_2CH(CH_3)_2$ |

TABLE II-continued

Compounds of the formula:

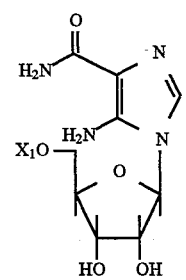

| Compound | $X_1$ |
|---|---|
| 37 | $-\overset{O}{\underset{\|}{C}}OCH_2C_6H_5$ |
| 38 | $-\overset{O}{\underset{\|}{C}}-\text{(3-pyridyl)}$ |

TABLE II-continued

Compounds of the formula:

[Structure: nucleoside with H2N-C(=O)- group, H2N, X1O-CH2-, HO, OH, imidazole ring with N and N]

| Compound | X₁ |
|---|---|
| 39 | −C(=O)−C₆H₄−O−C(=O)−C(CH₃)₃ |
| 40 | −C(=O)CH₂N(CH₃)₂ |
| 41 | −C(=O)CH₂−N(piperidine) |
| 42 | −C(=O)CH₂CH₃ |

TABLE II-continued

Compounds of the formula:

[Structure: same nucleoside]

| Compound | X₁ |
|---|---|
| 43 | −C(=O)CH₂CH₂CH₃ |
| 44 | −C(=O)CH₂CH₂CNH₂ |

TABLE III

Compounds of the formula

[Structure: nucleoside with X1O−, X3O, OX2 substituents]

| Compound | X₁ | X₂ | X₃ |
|---|---|---|---|
| 45 | −C(=O)−O−(cyclohexyl with CH(CH₃)₂ and CH₃ substituents) | −H | −H |

TABLE III-continued
Compounds of the formula
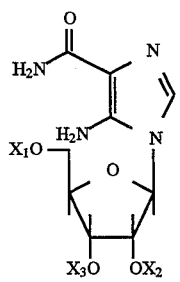
| Compound | X₁ | X₂ | X₃ |
|---|---|---|---|
| 46 | —H | —H | —C(=O)O-cyclohexyl with 2-CH₃, 5-CH(CH₃)₂ |
| 47 | —C(=O)O-cyclopropyl | —H | —H |
| 48 | —H | —H | —CO-O-cyclopropyl |
| 49 | —COCH₂CH₂OCH₃ | —H | —H |
| 50 | —H | —H | —C(=O)—O—CH₂CH₂OCH₃ |
| 51 | —COCH₂CH₂—O—phenyl | —H | —H |
| 52 | —H | —H | —COCH₂CH₂O—phenyl |
| 53 | —C(=O)O-(γ-butyrolactone-3-yl) | —H | —H |
| 54 | —H | —H | —CO-O-(γ-butyrolactone-3-yl) |

TABLE IV

| Treatment | Tissue Concentration (nMoles/g) | | |
|---|---|---|---|
| | Adenosine | AICA Riboside | ZMP |
| Control (Saline) | 272 ± 31 | 0 | 0 |
| AICA-riboside | 409 ± 60 | 774 ± 73 | 385 ± 15 |
| Prodrug A | 553 ± 46 | 592 ± 55 | 161 ± 9 |

TABLE V

Protection against Ischemic Injury in Skin Flap

| Treatment | Number Evaluated | % Viable |
|---|---|---|
| Control | 24 | 33 |
| AICA riboside | 8 | 75 |
| AICA riboside + ADA | 7 | 43 |
| SOD | 18 | 68 |

TABLE VI

| RABBIT | PRE-DOSE | 2H POST-DOSE | CHANGE(+/−) |
|---|---|---|---|
| AICA Riboside - 2 ml(100 mg/kg) - Blood Glucose - mg % | | | |
| 1 | 111 | 87 | −24 |
| 2 | 117 | 89 | −28 |
| 3 | 113 | 89 | −24 |
| 4 | 112 | 122 | +10 |
| 5 | 118 | 96 | −22 |
| 6 | 121 | 98 | −23 |
| 7 | 117 | 106 | −11 |
| 8 | 152 | 99 | −53 |
| 9 | 118 | 93 | −25 |
| 10 | 113* | 215* | +102* |
| Mean | 120 | 98 | −22 |
| AICA Riboside - 4 ml(200 mg)/kg Blood Glucose - mg % | | | |
| 1 | 114 | 100 | −14 |
| 2 | 108 | 32** | −76 |
| 3 | 121 | 79 | −42 |
| 4 | 125 | 56 | −69 |
| 5 | 121 | 12 | −59 |
| Mean | 118 | 66 | −52 |

*Values considered outliers due to hemolysis of 2h sample were not included in mean.
**Rabbit convulsed and was sacrificed.

TABLE VII

IC50 for Inhibition of FDPase by ZMD

| Species | IC50 (μM) |
|---|---|
| Dog | 90 |
| Gerbil | 50 |
| Guinea Pig | 12 |
| Human | 48 |
| Mouse | 150 |
| Rabbit | 41 |
| Rat | 375 |

TABLE VIII

BIOAVAILABILITY

| Compound | Tmax (hr) | Cmax(ug/ml) | AUC(μg · hr/ml) | F(%) |
|---|---|---|---|---|
| AICA riboside (i.v.) | — | — | 8.3 | 100 |
| AICA riboside (oral) | 0.75 | 1.1 | 0.9 | 11 |
| CI*(2',3',5'-Triacetyl-AICA riboside | 1.5 | 2.2 | 3.2 | 39 |
| 10*(5'-isobutyryl-AICA riboside | 0.75 | 5.0 | 4.9 | 60 |
| 11*(5'-pivalyl-AICA riboside | 1.0 | 3.2 | 3.7 | 44 |

*Compounds from Table I

We claim:

1. A method of lowering blood glucose levels in patients in need thereof, which comprises administering to said patients a pharmaceutically acceptable blood glucose lowering amount of a fructose-1,6-diphosphatase inhibitor which binds to the AMP site of fructose-1,6-diphosphatase.

2. The method of claim 1 wherein said inhibitor comprises a purine nucleoside, a purine nucleoside analog or prodrug thereof.

3. The method of claim 2 wherein said inhibitor is an AICA riboside prodrug which comprises a modified AICA riboside having an AICA ribosyl moiety and at least one hydrocarbyloxycarbonyl or hydrocarbylcarbonyl moiety.

4. The method of claim 3 comprising administering an AICA riboside prodrug of the formula:

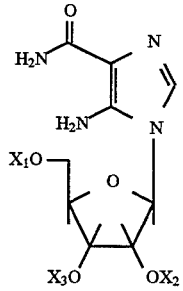

wherein $X_1$, $X_2$ and $X_3$ are independently (a) hydrogen, (b)

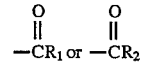

wherein $R_1$ is independently hydrocarbyl or mono- or dihydrocarbylamino and $R_2$ is independently hydrocarbyl, or (c) two of $X_1$, $X_2$, and $X_3$ taken together form a cyclic carbonate group.

5. The method of claim 4 wherein $X_1$ is

$X_2$ is hydrogen or

and $X_3$ is hydrogen or

6. The method of claim 5, wherein $X_1$, $X_2$ and $X_3$ are all acetyl.

7. A method of treating patients for whom a lowered blood glucose level is desired comprising administering to said patient a therapeutically effective amount of AICA riboside.

8. A method of treating an animal with diabetes mellitus which comprises administering to said animal in need thereof a therapeutically effective amount of a fructose-1,6-diphosphatase inhibitor which binds to the AMP site of fructose-1,6-diphosphatase.

9. A method of inhibiting gluconeogenesis in an animal, which comprises administering to said animal in need thereof a therapeutically effective amount of a fructose-1,6-diphosphatase inhibitor which binds to the AMP site of fructose-1,6-diphosphatase.

10. The method of any one of claims 1–9, wherein said patient is hyperglycemic.

11. The method of any one of claims 1–9, wherein said patient is insulin resistant.

12. The method of any one of claims 1–9, wherein said patient is diabetic.

13. The method of any one of claims 1–9, wherein said patient is a Syndrome X patient.

14. The method of any one of claims 1–9, wherein said patient is receiving total parenteral nutrition.

15. A method of lowering blood glucose in an animal by inhibiting the AMP site of fructose-1,6-diphosphatase which comprises administering to said animal a therapeutically effective amount of an agent which enhances hepatic ZMP.

16. The method of claim 8 wherein said inhibitor comprises a purine nucleoside, a purine nucleoside analog, or prodrug thereof.

17. The method of claim 16 wherein said inhibitor comprises AICA riboside or an AICA riboside prodrug.

18. The method of claim 9 wherein said inhibitor comprises a purine nucleoside, a purine nucleoside analog, or prodrug thereof.

19. The method of claim 16 wherein said purine nucleoside, purine nucleoside analog, or prodrug thereof is or becomes mono-phosphorylated in the position corresponding to the 5'-position on AICA riboside.

20. The method according to claim 18 wherein said inhibitor comprises AICA riboside or an AICA riboside prodrug.

21. The method of claim 17 wherein said prodrug comprises a modified AICA riboside having an AICA ribosyl moiety and at least one hydrocarbyloxycarbonyl or hydrocarbylcarbonyl moiety.

22. The method of claim 20 wherein said prodrug comprises a modified AICA riboside having an AICA ribosyl moiety and at least one hydrocarbyloxycarbonyl or hydrocarbylcarbonyl moiety.

* * * * *